United States Patent [19]
Mulvihill et al.

[11] Patent Number: 5,648,254
[45] Date of Patent: Jul. 15, 1997

[54] CO-EXPRESSION IN EUKARYOTIC CELLS

[75] Inventors: Eileen R. Mulvihill, Seattle, Wash.; A. Ashok Kumar, Flemington, N.J.

[73] Assignee: ZymoGenetics, Inc., Seattle, Wash.

[21] Appl. No.: 275,076

[22] Filed: Jul. 14, 1994

Related U.S. Application Data

[63] Continuation of Ser. No. 785,865, Oct. 28, 1991, abandoned, which is a continuation of Ser. No. 445,302, Dec. 4, 1989, abandoned, which is a continuation-in-part of Ser. No. 144,357, Jan. 15, 1988, abandoned.

[51] Int. Cl.$^6$ .............................. C12N 9/68; C12N 5/00; C12N 1/16; C12N 15/00
[52] U.S. Cl. .................. 435/217; 435/254.2; 435/172.3; 435/352
[58] Field of Search ................... 435/172.3, 69.1, 435/217, 240.2, 255, 320.1, 254.2

[56] References Cited

U.S. PATENT DOCUMENTS

| | | | |
|---|---|---|---|
| 4,517,294 | 5/1985 | Bock et al. | 435/70.1 |
| 4,704,362 | 11/1987 | Itakura et al. | 435/252.3 |
| 4,711,848 | 12/1987 | Insley et al. | 435/91 |
| 4,713,339 | 12/1987 | Levinson et al. | 435/240.2 |
| 4,929,553 | 5/1990 | Bussey et al. | 435/172.3 |
| 4,952,512 | 8/1990 | Loskutoff et al. | 435/320.1 |

FOREIGN PATENT DOCUMENTS

| | | | |
|---|---|---|---|
| 75754/87 | 1/1988 | Australia . | |
| 22099/88 | 4/1989 | Australia | C12N 15/00 |
| 072 925 | 3/1983 | European Pat. Off. | C12N 15/00 |
| 0 117 058 | 8/1984 | European Pat. Off. | C12N 15/00 |
| 174 835 | 3/1986 | European Pat. Off. | C12N 9/48 |
| 0 195 592 | 9/1986 | European Pat. Off. | C12N 15/00 |
| 0 200 421 | 12/1986 | European Pat. Off. | C12N 15/00 |
| 220 958 | 5/1987 | European Pat. Off. | C07K 3/10 |
| 253 455 | 1/1988 | European Pat. Off. | C12N 15/00 |
| 319 944 | 6/1989 | European Pat. Off. | C12N 15/00 |
| 84/01786 | 5/1984 | WIPO | A61K 37/54 |
| 85/01959 | 5/1985 | WIPO | C12P 21/00 |
| WO 87/04187 | 1/1987 | WIPO | C12P 21/02 |
| WO 87/06953 | 5/1987 | WIPO | C12N 15/00 |
| 87/03906 | 7/1987 | WIPO | C12N 15/00 |
| 88/05825 | 8/1988 | WIPO | C12P 21/00 |
| 88/08035 | 10/1988 | WIPO | C12P 21/02 |

OTHER PUBLICATIONS

P.A. Andreasen, et al., Plasminogen activator inhibitor type–1: reactive center and amino–terminal heterogeneity determined by protein and eDNA sequencing; *Federation of European Biochemical Societies*, vol. 209, No. 2, p. 213, Dec. 1986.
William E. Holmes, et al., Primary Structure of Human $a_2$–Antiplasmin, a Serine Protease Inhibitor (Serpin), *The Journal of Biological Chemistry*, vol. 262, No. 4, pp. 1659–1664, Feb. 5, 1987.
Dorner et al., "The Relationship of N–linked Glycosylation and Heavy Chain–binding Protein Association with the Secretion of Glycoproteins," *J. Cell. Biol.* 105:2665–2674, 1987.
Fuller et al., "The *Saccharomyces cerevisiae* KEX2 Gene ..." in L. Leive (ed.), *Microbiology* 1986, American Society for Microbiology, Washington, D.C., pp. 273–278, 1986.
Kaufman et al., "Expression, Purification and Characterization of Recombinant γ–Carboxylated Factor IX ..." *J. Biol. Chem.* 261:9622–9628, 1986.
Anson et al., "Expression of active human clotting factor IX from recombinant DNA clones in mammalian cells," *Nature* 315:683–685, 1985.
Busby et al., "Expression of active human factor IX in transfected cells," *Nature* 316:271–273, 1985.
Kurachi et al., "Isolation and characterization of a cDNA coding for human factor IX," *Proc. Natl. Acad. Sci. USA* 79:6461–6464, 1982.
Malinowski et al., "Characterization of a Complementary Deoxyribonucleic Acid Coding for Human and Bovine Plasminogen," *Biochemistry* 23:4243–4250, 1984.
Forsgren et al., "Molecular cloning and characterization of a full–length cDNA clone for human plasminogen," *FEBS Lett.* 213:254–260, 1987.
Long et al., "Complete Sequence of the cDNA for Human $\alpha_1$–Antitrypsin and the Gene for the S Variant," *Biochemistry* 23: 4828–4837, 1984.
Foster et al., "The nucleotide sequence of the gene for human protein C," *Proc. Natl. Acad. Sci. USA* 82:4673–4677, 1985.
Degen et al., "Characterization of the Complementary Deoxyribonucleic Acid and Gene Coding for Human Prothrombin," *Biochemistry* 22:2087–2097, 1983.
Toole et al., "Molecular cloning of a cDNA encoding human antihaemophilic factor," *Nature* 312:342–347, 1984.
Lynch et al., "Molecular Cloning of the cDNA for Human von Willebrand Factor: Authentication by a New Method," *Cell* 41:49–56, 1985.
Collins et al., "Molecular cloning of the human gene for von Willebrand factor and identification ... " *Proc. Natl. Acad. Sci. USA* 84:4393–4397, 1987.
Munro et al., "An Hsp70–like Protein in the ER: Identity with the 78 kd Glucose–Regulated Protein ... " *Cell* 46:291–300, 1986.
Spicer et al., "Isolation of cDNA clones coding for human tissue factor: Primary structure of the protein and cDNA," *Proc. Natl. Acad. Sci. USA* 84:5148–5152, 1987.

(List continued on next page.)

*Primary Examiner*—Nancy T. Vogel
*Attorney, Agent, or Firm*—Townsend and Townsend and Crew LLP

[57] ABSTRACT

A method of producing proteins of interest is disclosed. The method includes the introduction of a first DNA sequence encoding the protein of interest and at least one additional DNA sequence encoding a protein which processes or stabilizes the protein of interest into a eukaryotic host cell. The host cell is subsequently cultured under conditions which allow the DNA sequences to be expressed. Suitable eukaryotic hosts include mammalian cells and yeast cells.

15 Claims, 17 Drawing Sheets

OTHER PUBLICATIONS

Leytus et al., "Gene for Human Factor X: A Blood Coagulation Factor Whose Gene Organization Is Essentially Identical with That of Factor IX . . . " *Biochemistry* 25:5098–5102, 1986.

Pennica et al., "Cloning and expression of human tissue-type plasminogen activator cDNA in *E. coli*," *Nature* 301:214–221, 1983.

Kettner et al., "Inactivation of Trypsin–like Enzymes with Peptides of Arginine Chloromethyl Ketone," *Meth. Enzymol.* 80:826–842, 1981.

Folk et al., "Polyamines as physiological substrates for transglutaminases," *Chem. Abstr. 7–Enzymes* 93:40291x (1980).

Traus et al., Methods in Enzymology, vol. 80, pp. 754–765 (1981).

Scopes, Protein Purification, 1987, pp. 93–140, and 186–198, Springer–Verlag, New York.

Carrell and Travis, "$\alpha_1$–Antitrypsin and the serpins: variation and countervariation," *TIBS*: 20–24, Jan. 1985.

Kaufman et al., "Effect of von Willebrand Factor Coexpression on the Synthesis and Secretion of Factor VIII in Chinese Hamster Ovary Cells," *Mol. Cell. Biol.* 9(3):1233–1242 1989.

Foster and Davie, "Characterization of a cDNA coding for human protein C," *Biochemistry* 81:4766–4770, 1984.

```
                10            20                      36                        51
       GCACTGCTGG CCAGTCCCAA A ATG GAA CAT AAG GAA GTG GTT CTT CTA CTT CTT TTA
                              MET Glu His Lys Glu Val Val Leu Leu Leu Leu Leu 66                      81                      96                     111
       TTT CTG AAA TCA GGT CAA GGA GAG CCT CTG GAT GAC TAT GTG AAT ACC CAG GGG
       Phe Leu Lys Ser Gly Gln Gly Glu Pro Leu Asp Asp Tyr Val Asn Thr Gln Gly 126                     141                     156
       GCT TCA CTG TTC AGT GTC ACT AAG AAG CAG CTG GGA GCA GGA AGT ATA GAA GAA
       Ala Ser Leu Phe Ser Val Thr Lys Lys Gln Leu Gly Ala Gly Ser Ile Glu Glu 171                     186                     201                     216
       TGT GCA GCA AAA TGT GAG GAG GAC GAA GAA TTC ACC TGC AGG GCA TTC CAA TAT
       Cys Ala Ala Lys Cys Glu Glu Asp Glu Glu Phe Thr Cys Arg Ala Phe Gln Tyr 231                     246                     261
       CAC AGT AAA GAG CAA CAA TGT GTG ATA ATG GCT GAA AAC AGG AAG TCC TCC ATA
       His Ser Lys Glu Gln Gln Cys Val Ile MET Ala Glu Asn Arg Lys Ser Ser Ile 276                     291                     306                     321
       ATC ATT AGG ATG AGA GAT GTA GTT TTA TTT GAA AAG AAA GTG TAT CTC TCA GAG
       Ile Ile Arg MET Arg Asp Val Val Leu Phe Glu Lys Lys Val Tyr Leu Ser Glu 336                     351                     366                     381
       TGC AAG ACT GGG AAT GGA AAG AAC TAC AGA GGG GCG ATG TCC AAA ACA AAA AAT
       Cys Lys Thr Gly Asn Gly Lys Asn Tyr Arg Gly Thr MET Ser Lys Thr Lys Asn 396                     411                     426
       GGC ATC ACC TGT CAA AAA TGG AGT TCC ACT TCT CCC CAC AGA CCT AGA TTC TCA
       Gly Ile Thr Cys Gln Lys Trp Ser Ser Thr Ser Pro His Arg Pro Arg Phe Ser 441                     456                     471                     486
       CCT GCT ACA CAC CCC TCA GAG GGA CTG GAG GAG AAC TAC TGC AGA AAT CCA GAC
       Pro Ala Thr His Pro Ser Glu Gly Leu Glu Glu Asn Tyr Cys Arg Asn Pro Asp 501                     516                     531
       AAC GAT CCG CAG GGG CCC TGG TGC TAT ACT ACT GAT CCA GAA AAG AGA TAT GAC
       Asn Asp Pro Gln Gly Pro Trp Cys Tyr Thr Thr Asp Pro Glu Lys Arg Tyr Asp 546                     561                     576                     591
       TAC TGC GAC ATT CTT GAG TGT GAA GAG GAA TGT ATG CAT TGC AGT GGA GAA AAC
       Tyr Cys Asp Ile Leu Glu Cys Glu Glu Glu Cys MET His Cys Ser Gly Glu Asn 606                     621                     636                     651
       TAT GAC GGC AAA ATT TCC AAG ACC ATG TCT GGA CTG GAA TGC CAG GCC TGG GAC
       Tyr Asp Gly Lys Ile Ser Lys Thr MET Ser Gly Leu Glu Cys Gln Ala Trp Asp 666                     681                     696
       TCT CAG AGC CCA CAC GCT CAT GGA TAC ATT CCT TCC AAA TTT CCA AAC AAG AAC
       Ser Gln Ser Pro His Ala His Gly Tyr Ile Pro Ser Cys Phe Pro Asn Lys Asn
```

FIG. 6A

```
    711                  726                  741                  756
CTG AAG AAG AAT TAC TGT CGT AAC CCC GAG AGG GAG CTG CGC CCT TGG TGT TTC
Leu Lys Lys Asn Tyr Cys Arg Asn Pro Glu Arg Glu Leu Arg Pro Trp Cys Phe 771                  786                  801
ACC ACC GAC CCC AAC AAG GCG TGG GAA CTT TGT GAC ATC CCC CGC TGC ACA ACA
Thr Thr Asp Pro Asn Lys Arg Trp Glu Leu Cys Asp Ile Pro Arg Cys Thr Thr 816                  831                  846                  861
CCT CCA CCA TCT TCT GGT CCC ACC TAC CAG TGT CTG AAG GGA ACA GCT GAA AAC
Pro Pro Pro Ser Ser Gly Pro Thr Tyr Gln Cys Leu Lys Gly Thr Gly Glu Asn 876                  891                  906                  921
TAT CGC GGG AAT GTG GCT GTT ACC CTG TCC GGG CAC ACC TGT CAG CAC TGG AGT
Tyr Arg Gly Asn Val Ala Val Thr Val Ser Gly His Thr Cys Gln His Trp Ser 936                  951                  966
GCA CAG ACC CCT CAC ACA CAT AAC AGG ACA CCA GAA AAC TTC CCC TGC AAA AAT
Ala Gln Thr Pro His Thr His Asn Arg Thr Pro Glu Asn Phe Pro Cys Lys Asn 981                  996                  1011                 1026
TTG GAT GAA AAC TAC TGC CGC AAT CCT GAC GGA AAA AGG GCC CCA TGG TGC CAT
Leu Asp Glu Asn Tyr Cys Arg Asn Pro Asp Gly Lys Arg Ala Pro Trp Cys His 1401                 1056                 1071
ACA ACC AAC AGC CAA GTG CGG TGG GAG TAC TGT AAG ATA CCG TCC TGT GAC TCC
Thr Thr Asn Ser Gln Val Arg Trp Glu Tyr Cys Lys Ile Pro Ser Cys Asp Ser 1086                 1101                 1116                 1131
TCC CCA GTA TCC ACG GAA CAA TTG GCT CCC ACA GCA CCA CCT GAG CTA ACC CCT
Ser Pro Val Ser Thr Glu Gln Leu Ala Pro Thr Ala Pro Pro Glu Leu Thr Pro 1146                 1161                 1176                 1191
GTG GTC CAG GAC TGC TAC CAT GGT GAT GGA CAG AGC TAC CGA GGC ACA TCC TCC
Val Val Gln Asp Cys Tyr His Gly Asp Gly Gln Ser Tyr Arg Gly Thr Ser Ser 1206                 1221                 1236
ACC ACC ACC ACA GSA AAG AAG TGT CAG TCT TGG TCA TCT ATG ACA CCA CAC CGG
Thr Thr Thr Thr Gly Lys Lys Cys Gln Ser Trp Ser Ser MET Thr Pro His Arg 1251                 1266                 1281                 1296
CAC CAG AAG ACC CCA GAA AAC TAC CCA AAT GCT GGC CTG ACA ATG AAC TAC TGC
His Gln Lys Thr Pro Glu Asn Tyr Pro Asn Ala Gly Leu Thr MET Asn Tyr Cys 1311                 1326                 1341
AGG AAT CCA GAT GCC GAT AAA GGC CCC TGG TGT TTT ACC ACA GAC CCC AGC GTC
Arg Asn Pro Asp Ala Asp Lys Gly Pro Trp Cys Phe Thr Thr Asp Pro Ser Val 1356            1371                 1386                 1401
AGG TGG GAG TAC TGC AAC CTG AAA AAA TGC TCA GGA ACA GAA GCG AGT GTT GTA
Arg Trp Glu Tyr Cys Asn Leu Lys Lys Cys Ser Gly Thr Glu Ala Ser Val Val
```

FIG. 6B

```
     1416              1431              1446              1461
GCA CCT CCG CCT GTT GTC CTG CTT CCA GAT GTA GAG ACT CCT TCC GAA GAA GAC
Ala Pro Pro Pro Val Val Leu Leu Pro Asp Val Glu Thr Pro Ser Glu Glu Asp 1476              1491              1506
TGT ATG TTT GGG AAT GGG AAA GGA TAC CGA GGC AAG AGG GCG ACC ACT GTT ACT
Cys MET Phe Gly Asn Gly Lys Gly Tyr Arg Gly Lys Arg Ala Thr Thr Val Thr 1521              1536              1551              1566
GGG ACG CCA TGC CAG GAC TGG GCT GCC CAG GAG CCC CAT AGA CAC AGC ATT TTC
Gly Thr Pro Cys Gln Asp Trp Ala Ala Gln Glu Pro His Arg His Ser Ile Phe 1581              1596              1611
ACT CCA GAG ACA AAT CCA CGG GCG GGT CTG GAA AAA AAT TAC TGC CGT AAC CCT
Thr Pro Glu Thr Asn Pro Arg Ala Gly Leu Glu Lys Asn Tyr Cys Arg Asn Pro 1626              1641              1656              1671
GAT GGT GAT GTA GGT GGT CCC TGG TGC TAC ACG ACA AAT CCA AGA AAA CTT TAC
Asp Gly Asp Val Gly Gly Pro Trp Cys Tyr Thr Thr Asn Pro Arg Lys Leu Tyr 1686              1701              1716              1731
GAC TAC TGT GAT GTC CCT CAG TGT GCG GCC CCT TCA TTT GAT TGT GGG AAG CCT
Asp Tyr Cys Asp Val Pro Gln Cys Ala Ala Pro Ser Phe Asp Cys Gly Lys Pro 1746              1761              1776
CAA GTG GAG CCG AAG AAA TGT CCT GGA AGG GTT GTA GGG GGG TGT GTG GCC CAC
Gln Val Glu Pro Lys Lys Cys Pro Gly Arg Val Val Gly Gly Cys Val Ala His 1791              1806              1821              1836
CCA CAT TCC TGG CCC TGG CAA GTC AGT CTT AGA ACA AGG TTT GGA ATG CAC TTC
Pro His Ser Trp Pro Trp Gln Val Ser Leu Arg Thr Arg Phe Gly MET His Phe 1851              1866              1881
TCT GGA GGC ACC TTG ATA TCC CCA CAG TGG GTG TTG ACT GCT GCC CAC TGC TTG
Cys Gly Gly Thr Leu Ile Ser Pro Gln Trp Val Leu Thr Ala Ala His Cys Leu 1896              1911              1926              1941
GAG AAG TCC CCA AGG CCT TCA TCC TAC AAG GTC ATC CTG GGT GCA CAC CAA GAA
Glu Lys Ser Pro Arg Pro Ser Ser Tyr Lys Val Ile Leu Gly Ala His Gln Glu 1956              1971              1986              2001
GTG AAT CTC GAA CCG CAT GTT CAG GAA ATA GAA GTG TCT AGG CTG TTG TTG GAG
Val Asn Leu Glu Pro His Val Gln Glu Ile Glu Val Ser Arg Leu Phe Leu Glu 2016              2031              2046
CCC ACA CGA AAA GAT ATT GCC TTG CTA AAG CTA AGC AGT CCT GCC GTC ATC ACT
Pro Thr Arg Lys Asp Ile Ala Leu Leu Lys Leu Ser Ser Pro Ala Val Ile Thr 2061              2076              2091              2106
GAC AAA GTA ATC CCA GCT TGT CTG CCA TCC CCA AAT TAT GTG GTC GCT GAC CGG
Asp Lys Val Ile Pro Ala Cys Leu Pro Ser Pro Asn Tyr Val Val Ala Asp Arg
```

FIG. 6C

```
                    2121                    2136                    2151
        ACC GAA TGT TTC ATC ACT GGC TGG GGA GAA ACC CAA GCT ACT TTT GGA GCT GGC
        Thr Glu Cys Phe Ile Thr Gly Trp Gly Glu Thr Gln Gly Thr Phe Gly Ala Gly 2166                    2181                    2196                    2211
        CTT CTC AAG GAA GCC CAG CTC CCT GTG ATT GAG AAT AAA GTG TGC AAT CGC TAT
        Leu Leu Lys Glu Ala Gln Leu Pro Val Ile Glu Asn Lys Val Cys Asn Arg Tyr 2226                    2241                    2256                    2271
        GAG TTT CTG AAT GGA AGA GTC CAA TCC ACC GAA CTC TGT GCT GGG CAT TTG GCC
        Glu Phe Leu Asn Gly Arg Val Gln Ser Thr Glu Leu Cys Ala Gly His Leu Ala 2286                    2301                    2316
        GGA GGC ACT GAC AGT TGC CAG GGT GAC AGT GGA GGT CCT CTG GTT TGC TTC GAG
        Gly Gly Thr Asp Ser Cys Gln Gly Asp Ser Gly Gly Pro Leu Val Cys Phe Glu 2331                    2346                    2361                    2376
        AAG GAC AAA TAC ATT TTA CAA GGA GTC ACT TCT TGG GGT CTT GGC TGT GCA CGC
        Lys Asp Lys Tyr Ile Leu Gln Gly Val Thr Ser Trp Gly Leu Gly Cys Ala Arg 2391                    2406                    2421
        CCC AAT AAG CCT GGT GTC TAT GTT CGT GTT TCA AGG TTT GTT ACT TGG ATT GAG
        Pro Asn Lys Pro Gly Val Tyr Val Arg Val Ser Arg Phe Val Thr Trp Ile Glu 2436        2451                 2464        2474        2484        2494
        GGA GTG ATG AGA AAT AAT TAA TTGGACGGGA GACAGAGTGA CGCACTGACT CACCTAGAGG
        Gly Val MET Arg Asn Asn 2504       2514       2524       2534       2544       2554       2564
        CTGGAACGAG GGTAGGGATT TAGCATGCTG GAAATAACTG GCAGTAATCA AACGAAGACA CTGTCCCCAG 2574       2584       2594       2604       2614       2624       2634
        CTACCAGCTA CGCCAAACCT CGGCATTTTT TGTGTTATTT TCTGACTGCT GGATTCTGTA GTAAGGTGAC 2644       2654       2664       2674
        ATAGCTATGA CATTTGTTAA AAATAAACTC TGTACTTAAC TTTGA
```

FIG. 6D

CO-EXPRESSION IN EUKARYOTIC CELLS

CROSS-REFERENCE TO RELATED APPLICATIONS

This application is a continuation of U.S. patent application Ser. No. 07/785,865, filed Oct. 28, 1991, now abandoned; which is a continuation of U.S. patent application Ser. No. 07/445,302, filed Dec. 4, 1989, now abandoned; which is a continuation in part of U.S. patent application Ser. No. 07/144,357, filed Jan. 15, 1988, now abandoned.

TECHNICAL FIELD

The present invention relates generally to the production of proteins, and more particularly, to the production of proteins in biologically active form and in economically feasible amounts.

BACKGROUND OF THE INVENTION

Recombinant DNA technology has been used to produce a variety of proteins of therapeutic or other economic value, including enzymes, growth factors and peptide hormones. These proteins have been produced in bacteria, fungal cells and, more recently, cultured mammalian cells. Because single-celled organisms cannot correctly process many human proteins, it has often been necessary to use cultured mammalian cells to make these proteins.

Mammalian cells can be transfected to express cloned DNA by well-established laboratory procedures. However, not all mammalian cell types will efficiently express transfected DNA sequences, and cells which have been shown to be efficient expressers of one transfected sequence will in other cases produce only low levels of other gene products. Low expression levels for transfected genes may be associated with degradation of the protein product intra- and/or extra-cellularly, production of inactive form(s) of the protein or production of form(s) of the protein that are cytotoxic. Low levels of protein or activity may also result from an unstable mRNA sequence, proteolytic activation or inadequate, inefficient or improper processing by the host cell. Processing steps which may be necessary for the activity or secretion of a newly synthesized protein include specific proteolytic cleavage, subunit polymerization, disulfide bond formation, post-translational or co-translational modification of certain amino acids and glycosylation.

These problems in protein production reflect the specialized nature of cells derived from higher organisms. Mammalian cells derived from a particular tissue may not properly produce a protein not normally made by that tissue. In addition, mammalian cell lines adapted to grow in culture are derived from tumors or are otherwise abnormal, often leading to unpredictable protein processing. For example, a number of research groups have produced human coagulation factor IX in cultured mammalian cells (Kaufman et al., *J. Biol. Chem.* 261:9622–9628, 1986; Anson et al., *Nature* 315:683–685, 1985; Hagen et al., EP 200,421; Busby et al., *Nature* 316:271–273, 1985). Despite efforts to maximize production of biologically active protein through the use of strong promoters, enhancers, increased gene copy number, etc., and despite the relatively high levels of factor IX mRNA observed, levels of active factor IX produced by these transfected cell lines do not exceed about 5 µg/ml of cell culture medium. In some cases, precursor forms of factor IX are made but mature protein is ineffectively secreted from the host cell.

Problems with protein production have previously been dealt with by experimenting with a number of different cell types and by selecting and screening a large number of isolates of a particular transformed or transfected strain or cell line. Such an approach is extremely labor intensive and carries no assurance of success. Consequently, there is a need in the art for a method of systematically and predictably producing recombinant cells which can express proteins of interest in an active form and in economically feasible amounts. The present invention provides such a system, and further provides other related advantages.

DISCLOSURE OF THE INVENTION

Briefly stated, the present invention provides a method of producing a protein of interest comprising the steps of (a) introducing into a eukaryotic host cell a first DNA sequence encoding the protein of interest and at least one additional DNA sequence, the additional DNA sequence encoding a protein which processes or stabilizes the protein of interest, wherein said DNA sequences are operably linked to transcriptional promoter and terminator sequences; (b) culturing the host cell under conditions which allow the first DNA sequence and the. additional DNA sequence(s) to be expressed; and (c) isolating the protein of interest from the host cell. The step of introducing the DNA sequences into the host cell may be through (a) cotransfection or cotransformation with multiple vectors, each containing a separate expression unit; or (b) transfection or transformation with a single vector containing multiple expression units. When the host cell is a mammalian host cell, the step of introducing may also be through transfection with a single vector containing a single expression unit that is transcribed into a polycistronic message. When yeast host cells are utilized, a preferred method for introducing the DNA sequences comprises (a) transforming the yeast host cell with a single expression unit containing the additional DNA sequence(s); (b) isolating host cells which stably produce the processing or stabilizing activity; and (c) transforming the isolated host cells with the first DNA sequence encoding the protein of interest. Preferably, the initial transforming step results in the integration of the single expression unit into the yeast host cell genome.

Preferred first DNA sequences include those encoding plasma serine proteases such as t-PA, factor VII, factor IX, factor X, protein C and plasminogen. Preferred additional DNA sequences include those encoding proteases, protease inhibitors, gamma-carboxylase, and proteins which bind to the protein of interest.

In another aspect of the present invention, eukaryotic host cells into which a DNA sequence encoding a protein or interest as described above and one or more additional DNA sequences encoding a protein or proteins which process or stabilize the protein of interest as described above have been introduced are disclosed. Preferred eukaryotic host cells include mammalian host cells and yeast host cells.

These and other aspects of the present invention will become evident upon reference to the following detailed description and attached drawings.

BRIEF DESCRIPTION OF THE DRAWINGS

FIG. 6 illustrates the nucleotide sequence of a plasminogen cDNA, together with the encoded amino acid sequence.

BEST MODE FOR CARRYING OUT THE INVENTION

Figure 1:
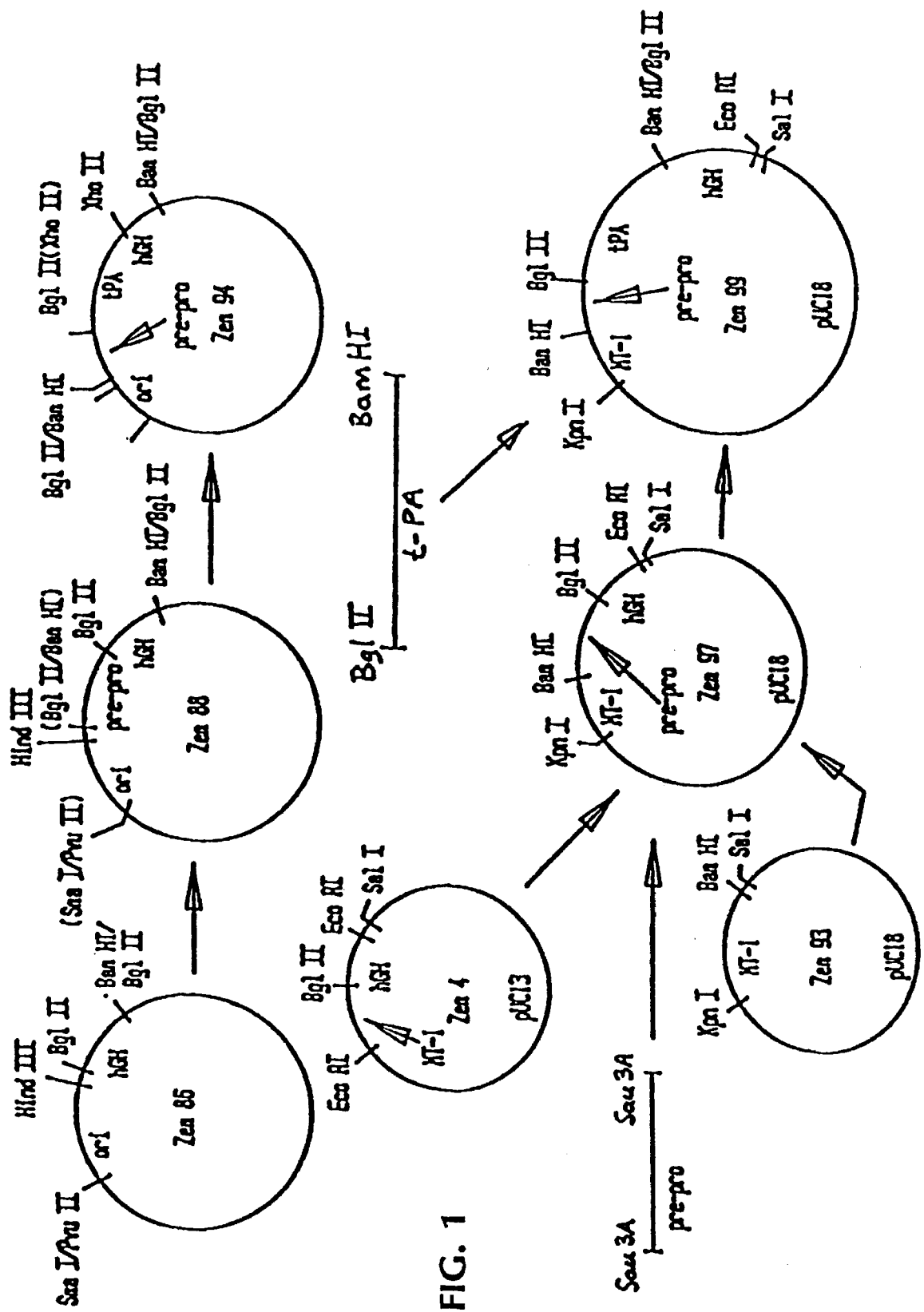
FIG. 1 illustrates the construction of the plasmid Zem99.

Prior to setting forth the invention, it may be helpful to an understanding thereof to set forth definitions of certain terms to be used hereinafter.

Expression unit: A cloned DNA sequence encoding a protein or polypeptide operably linked to transcriptional promoter and terminator sequences.

Stabilize: The term stabilize is used herein to denote the protection of a protein from degradation. Stabilization may proceed by a number of mechanisms, including inhibition of a proteolytic enzyme which would otherwise degrade the protein of interest, binding to the protein of interest to protect it from a proteolytic enzyme, and binding to or otherwise inhibiting the action of a cofactor or other molecule required for the activity of a protease.

Process: As used herein, "process" means to modify the structure of a protein. Processing of proteins includes such modifications as specific proteolytic cleavage to produce a multi-chain protein or remove peptides from protein precursors; modification of amino acids, including carboxylation and hydroxylation; and carbohydrate addition at specific sites. Processing may be necessary for full biological activity of a protein or may be required to enable the secretion of a protein from a cell.

Transfection and Transformation: The process of introducing cloned DNA into host cells. Transfection refers to inserting DNA into mammalian cell lines. The process of inserting DNA into fungal and bacterial cells is known as transformation. A number of transfection and transformation procedures are well known in the art.

As noted above, cells containing cloned DNA sequences do not always produce proteins encoded by those cloned sequences at economically feasible levels or in biologically active form. This is often due to the origin of the cell or its abnormal nature. In many instances, it may not be possible to obtain a cultured cell line or host cell strain with the necessary characteristics to enable it to produce a particular protein at the desired level. In any event, screening a large number of potential host cell lines may not be feasible and carries no assurance of success.

The present invention overcomes the shortcomings of available cells by providing a method of introducing into a eukaryotic host cell a gene or cDNA encoding a protein of interest together with one or more additional DNA sequences encoding a protein or proteins which process or stabilize the protein of interest. Processing proteins include proteases which cleave a precursor protein at a particular site to provide the mature and/or active form of the protein, for example peptidases which remove signal peptides or propeptides, or which cleave a single-chain polypeptide to a multi-chain form. Other examples of processing proteins are those which modify amino acids, such as gamma-carboxylase, an enzyme which modifies specific glutamic acid residues of certain clotting factors and other calcium binding proteins. Other processing proteins include enzymes responsible for the conversion of aspartic acid to β-hydroxy aspartic acid, a modification necessary for the activity of protein C, those responsible for the addition of carbohydrate chains to glycoproteins and those responsible for myristoylation, C-terminal amino acid removal, hydroxylation of proline residues, sulfation and C-terminal amidation. Stabilizing proteins include protease inhibitors which block the proteolytic degradation of the protein of interest; proteins which bind to the protein of interest making it unavailable as a substrate; proteins which bind to protein cofactors, ions, or other molecules required by a protease; and proteins which inactivate cofactors. It will be appreciated that a particular eukaryotic host cell can be transfected or transformed to produce several processing proteins, several stabilizing proteins, or a combination of stabilizing and processing proteins.

The present invention is based in part on the unexpected discovery that a variety of processing and stabilizing proteins will function outside their native environments. For example, it is disclosed herein that factor IX, an enzyme which normally functions in the blood, can activate factor VII intracellularly. Additionally, it has been found that the product of the yeast KEX2 gene functions normally within mammalian cells and that several forms of alpha-1-antitrypsin, when co-expressed with plasminogen, greatly enhance expression levels of intact plasminogen. The observed processing and stabilization indicate that both the protein of interest and the processing or stabilizing protein are unexpectedly targeted to the same cellular compartment. The observed function of these processing proteins is also surprising in view of the fact that the proteins of interest may not otherwise be produced in large amounts or in an intact or active form in a recombinant cell.

By characterizing a naturally occurring protein of interest and, as necessary, the gene or cDNA encoding it, one can deduce the nature of the processing steps involved in its biosynthesis. Characterization of the recombinant form of the protein will reveal whether or not it has been correctly processed and, if not, what processing steps were omitted. In accordance with the present invention, proper processing is provided through supplying the missing activity or augmenting a limiting activity. This activity may be supplied as the protein which normally processes the protein of interest, or as a related protein which normally performs a similar function in another context, such as a protein from a different cell type. An example of the latter case is the use of the yeast KEX2 gene to supply the processing protein which cleaves protein C or an activated protein C precursor to the two-chain form. Blocks in the secretion of a protein of interest can be determined by characterizing the intracellular and secreted forms of the recombinant protein. In this way, the missing or limiting processing step is determined.

In some instances, one will know the identity of the protein supplying the missing activity. In this case, the desired gene or cDNA is cloned and introduced into the chosen host cell.

When the protein responsible for the missing activity is not known, the protein of interest is analyzed, the nature of the missing processing step is determined, and a protein known to perform that function is selected. A suitable protein may be selected from known proteins with similar activity for which DNA sequences are available. Many such processing proteins have been characterized. For example, Kettner and Shaw (Meth. in Enzymology 80:826–842, 1981) have characterized the specificities of a number of proteases. Alternatively, a DNA sequence encoding the needed processing protein may be identified by transfecting cells with a mammalian expression library and selecting those cells that exhibit the needed activity.

Where protein stabilization is desired, cells transfected or transformed to produce the protein of interest are grown in the presence of various stabilizing proteins and assayed for production of the intact protein of interest. Generally, the cells will be labeled with a radioisotope and proteins will be analyzed by radioimmune precipitation and gel electrophoresis, or by other conventional techniques. The presence of the intact protein of interest in the culture medium indicates that the stabilizing protein is protecting the protein of interest from degradation. Stabilization may also lead to phenotypic changes in the host cell. For example, protease activity may cause cell detachment, which may be corrected by inhibiting that activity. Correction is indicated by the presence of the normal (adherent) phenotype. Alternatively, the breakdown products of the protein of interest are analyzed to determine the type of proteolysis responsible for the breakdown. Analysis of the amino sequence of the protein of interest will locate potential proteolytic processing sites, and appropriate protease inhibitors are selected and tested as described above or by transfecting the host cells to express the particular inhibitor (s).

When the desired processing or stabilizing protein has been identified, the DNA sequence encoding it and the DNA sequence encoding the protein of interest are introduced into chosen host cells as described below. It is preferred to first introduce the DNA sequence encoding the processing or stabilizing protein, select for cells expressing it, and then introduce the DNA sequence encoding the protein of interest; or to introduce both sequences in a single step. Cells expressing the introduced sequences are selected and screened for production of the protein of interest in the desired form or at the desired level. Cells which satisfy these criteria are then cloned and scaled up for production.

Proteins of interest which can be produced using the methods of the present invention include a variety of plasma serine proteases, such as coagulation factors VII, IX and X, activated factor VII (designated factor VIIa), activated factor X (factor Xa), protein C, activated protein C, protein S, tissue plasminogen activator (t-PA), plasminogen, and analogs and derivatives of these proteins, although virtually any protein of interest could be produced. The methods disclosed herein are particularly suited to the production of these serine proteases due to the post-translational processing necessary for their activity and/or secretion by the host cell.

According to the present invention, coagulation factors requiring gamma-carboxylation of specific glutamic acid residues for their biological activity may be secreted at high levels by cells into which has been introduced a DNA sequence encoding gamma-carboxylase. The gamma-carboxylation step has been found by the inventors to be limiting in mammalian cell lines commonly used for the production of recombinant coagulation factors. Furthermore, the present invention may permit the production of biologically active gamma-carboxylated proteins in non-mammalian host cells such as yeast cells.

Coagulation factor VII may be made in activated form by transfecting cells with DNA sequences encoding factor VII and factor IX. The precursor form of factor VII is activated by the factor IX and factor VIIa is secreted by the cells. Alternatively, a protein having the biological activity of factor VIIa may be produced by co-expressing a DNA sequence encoding a derivative or analog of factor VII and a DNA sequence encoding factor IX. DNA sequences encoding derivatives and analogs of factor VII are described in U.S. Pat. No. 4,784,950, which is herein incorporated by reference. As the activated form of factor VII has been shown to have therapeutic value, it would be desirable to produce the activated form directly. Direct production would increase yields, reduce the number of production steps and eliminate problems associated with activating blood products.

In another embodiment, a DNA sequence encoding protein C or a modified protein C precursor is inserted into a cell line which has been transfected to express the yeast KEX2 gene. This gene encodes an endopeptidase which cleaves after a dibasic amino acid sequence (Fuller et al., in Leive (ed.), Microbiology: 1986, 1986, pp. 273–278). Processing may be further enhanced by also transfecting the cells with the yeast KEX1 gene (Dmochowska et al., Cell 50:573–584, 1987), which encodes an enzyme which removes the basic amino acids from the C-terminus of the protein C light chain. Modified protein C precursors are described in pending commonly assigned U.S. Ser. Nos. 06/924,462 and 07/130,370 and related European Patent Office Publication 266,190, which are incorporated by reference herein in their entirety.

Activated protein C can also be produced in a cell line which has been transfected with DNA sequences encoding an activated protein C precursor, thrombin and thrombomodulin. The thrombin cleaves the activated protein C precursor (two-chain form of protein C) in the presence of thrombomodulin, and activated protein C is secreted by the cells. Activated protein C precursors are described in U.S. Ser. Nos. 06/924,462 and 07/130,370.

Factor VIIa and factor IXa can be produced in a cell line transfected to co-express factor X and factor VII or factor X and factor IX. The factor X cleaves the factor VII or factor IX, resulting in secretion of the activated clotting factor.

In yet another embodiment, the production of t-PA or a t-PA analog or derivative is enhanced by transfecting a host cell line to produce both t-PA or a t-PA analog or derivative and a protease inhibitor. Suitable protease inhibitors in this regard include TIMP (tissue inhibitor of metalloproteases), trypsin inhibitors and aprotinin, with aprotinin particularly preferred. Analogs and derivatives of t-PA are described in pending U.S. Ser. Nos. 06/822,005; 07/004,995; 07/053,411; 07/058,061; 07/058,217; 07/125,629; and 07/162,847 (related to European Patent Office Publications 293,936; 293,934; and 292,009; and Japanese Published Patent Application 63-133988). Expression of t-PA at commercially feasible levels has been difficult because the serine protease activity of t-PA results in detachment of cells from support surfaces. This necessitates the use of agents such as aprotinin in the growth media. The use of aprotinin in the media also allows the production of the single-chain form of t-PA, a desirable therapeutic product. However, aprotinin is both costly and limited in availability.

Plasminogen (including both glu-plasminogen and lys-plasminogen) can be produced in intact form using cells transfected to produce both plasminogen and a protease inhibitor. Variants of plasminogen (as described in U.S. patent application Ser. No. 053,412) may also be produced. Intracellular plasminogen activation and subsequent degradation have limited the ability to produce recombinant plasminogen at reasonable levels. Inhibition of plasminogen activation and/or plasmin activity by a co-expressed protease inhibitor will ameliorate this problem. A particularly preferred group of protease inhibitors in this regard is the serpins, including alpha-1-antitrypsin (AAT) and variants of alpha-1-antitrypsin (U.S. Pat. Nos. 4,711,848 and 4,732, 973). A particularly preferred AAT variant is the Argserpin Arg (358) alpha-1-antitrypsin, also known as the Pittsburgh mutant of alpha-1-antitrypsin (Owen et al., *N. Engl. J. Med.* 309:694–698, 1983). Other Argserpins, including plasminogen activator inhibitor 1 (PAI-1), antithrombin III and C1 inhibitor, may also be used. A DNA sequence encoding PAI-1 is disclosed by Andreasen et al. (*FEBS Lett.* 209:213–218, 1986). A DNA sequence encoding antithrombin III is disclosed by Bock et al. (U.S. Pat. No. 4,517,294). A cDNA encoding human C1 inhibitor is disclosed by Bock et al. (*Biochemistry* 25:4292–4301, 1986). Other protease inhibitors, such as $\alpha_2$ plasmin inhibitor ($\alpha_2$PI), may also be used. Combinations of protease inhibitors, such as $\alpha_2$PI and PAI-1, may also advantageously be co-expressed with plasminogen.

Other examples of protein-stabilizer combinations include stabilization of protein C by co-expression of protein S, stabilization of factor VIII by co-expression of von Willebrand factor and stabilization of factor VII by co-expression of tissue factor. BiP (Haas and Wabl, *Nature* 306:387–389, 1983) may also be used to stabilize various proteins. A cDNA encoding BiP is described by Munro and Pelham (*Cell* 46:291–300, 1986).

DNA sequences useful in carrying out the present invention may be cloned by standard procedures known in the art. Genomic or cDNA sequences may be used. Many such clones have been described in the literature, including DNAs encoding t-PA (Pennica et al., *Nature* 301:214–221, 1983), factor VII (Hagen et al., ibid.; Hagen et al., *Proc. Natl. Acad. Sci. USA* 83:2412–2416, 1986), factor IX (Kurachi and Davie, *Proc. Natl. Acad. Sci. USA* 79:6461–6464, 1982), plasminogen (Malinowski et al., *Biochemistry* 23:4243–4250, 1984; Forsgren et al., *FEBS Lett.* 213:254, 1987; Whitefleet-Smith et al., *Arch Biochem. Biophys.* 271:390–399, 1989), alpha-1-antitrypsin (Long et al., *Biochemistry* 23:4828–4837, 1984; Kawasaki, U.S. Pat. No. 4,559,311), protein C (Foster and Davie, *Proc. Natl. Acad. Sci. USA* 82:4673–4677, 1985), prothrombin (Friezner Degan et al., *Biochemistry* 22:2087–2097, 1983), factor VIII (Toole et al., *Nature* 312:342–347, 1984), von Willebrand factor (Lynch et al., *Cell* 41:49–56, 1985; Collins et al., *Proc. Natl. Acad. Sci. USA* 84:4393–4397, 1987), tissue factor (Spicer et al., *Proc. Natl. Acad. Sci. USA* 84:5148–5152, 1987) and factor X (Leytus et al., *Biochemistry* 25:5098–5102, 1986). Additional clones may be obtained by screening cosmid, genomic or cDNA libraries using as probes oligonucleotides designed on the basis of amino acid sequence data or cloned DNA fragments, or through the use of expression libraries which are screened with antibodies to the protein of interest (Young and David, *Proc. Natl. Acad. Sci. USA* 80:1194–1198, 1983), by ligand blotting (Sikela and Hahn, *Proc. Natl. Acad. Sci. USA* 84:3038–3042, 1987) or by assaying for activity.

The cloned DNA sequences are inserted into suitable expression vectors which are, in turn, used to transfect or transform suitable eukaryotic host cells.

Expression vectors for use in carrying out the present invention in mammalian cells will contain an expression unit comprising a promoter capable of directing the transcription of a cloned gene or cDNA introduced into a mammalian cell, the promoter being operably linked to the DNA sequence to be expressed. Viral promoters are preferred due to their efficiency in directing transcription. A particularly preferred promoter is the major late promoter from adenovirus 2. Other suitable promoters include the SV40 promoter (Subramani et al., *Mol. Cell Biol.* 1:854–864, 1981) and the MT-1 (metallothionein gene) promoter (Palmiter et al., *Science* 222:809–814, 1983). The expression unit will further comprise a transcriptional terminator downstream from and operably linked to the DNA sequence to be expressed. Such expression vectors may also contain a set of RNA splice sites located downstream from the promoter and upstream from the cloned DNA sequence or within the cloned sequence itself. Preferred RNA splice sites may be obtained from adenovirus and/or immunoglobulin genes. Also contained in the expression vectors is a polyadenylation signal, located downstream of the cloned DNA sequence. Particularly preferred are viral polyadenylation signals from SV40 or the polyadenylation signal from the adenovirus 5 Elb region. Terminators and polyadenylation signals may also be obtained from the gene encoding the protein of interest. Expression vectors useful in carrying out the present invention may also comprise a noncoding viral leader sequence, such as the adenovirus 2 tripartite leader, located between the promoter and the RNA splice sites. Preferred vectors may also include transcriptional enhancer sequences, such as the SV40 enhancer, and translational enhancer sequences, such as the sequences encoding the adenovirus VA RNAs.

Vectors containing cloned DNA sequences may then be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973) or electroporation (Neumann, *EMBO J.* 1:841–845, 1982). A small fraction of the cells integrate the DNA into the genome or maintain the DNA in non-chromosomal nuclear structures. In order to identify these integrants, a gene that confers a selectable phenotype (a selectable marker) is generally introduced into the cells along with the gene of interest. Preferred selectable markers include genes that confer resistance to drugs, such as neomycin, hygromycin, and methotrexate. If calcium phosphate-mediated transfection is used, selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing what is known as a dicistronic or polycistronic message. Constructs of this type are known in the art (for example, European Patent Office Publication No. 117,058; U.S. Pat. No. 4,713,339). Use of a single plasmid is generally preferred when using electroporation. After the cells have taken up the DNA, they are allowed to grow for a period of time, typically 1–2 days, to begin expressing the gene of interest. Drug selection is then applied to select for the growth of cells which are expressing the selectable marker. When using methotrexate selection, increasing the drug concentration allows selection for increased copy number of the cloned sequences, resulting in increased expression levels. Clones of such cells may be screened for production of the protein of interest. Useful screening methods include immunological assays and activity assays.

Preferred mammalian cell lines for use in the present invention include the COS (ATCC CRL 1650), BHK (ATCC CCL 10) and 293 (ATCC 1573) cell lines as well as derivatives and isolates of these cell lines, although other cell lines may be preferred for the production of particular proteins. A preferred BHK cell line is the tk⁻ts13 BHK cell line (Waechter and Baserga, Proc. Natl. Acad Sci. USA 79:1106–1110, 1982), hereinafter referred to as BHK 570 cells. A tk⁻ts13 BHK cell line is also available from the American Type Culture Collection under Accession Number CRL 1632. Other useful adherent cell lines include Rat Hep I (ATCC CRL 1600), Rat Hep II (ATCC CRL 1548), TCMK (ATCC CCL 139), Human Lung (ATCC CCL 75.1), Human hepatoma (ATCC HTB-52), Hep G2 (ATCC HB 8065), Mouse liver (ATCC CC 29.1) and DUKX cells (Urlaub and Chasin, Proc. Natl. Acad. Sci. USA 77:4216–4220, 1980). Useful suspension cell lines include AtT-20 (ATCC CCL 89), MOLT-4 (ATCC CRL 1582), BW5147.G.1.4.OUA$^R$.1 (ATCC CRL 1588), S194/5./XXO.BU.1 (ATCC TIB 20), EL4.BU.1.OUA$^r$.1.1 (ATCC TIB 41), Sp 2/0-Ag14 (ATCC CRL 1581), J558L (Oi et al., Proc. Natl. Acad. Sci. USA 80:825–829, 1983) and Raji (ATCC CCL 86).

In general, a host cell line will be selected on the basis of its ability to produce the protein of interest at a high level or its ability to carry out at least some of the processing steps necessary for the biological activity of the protein. In this way, the number of cloned DNA sequences which must be transfected into the host cell line may be minimized and overall yield of biologically active protein may be maximized. However, the present invention allows one to produce virtually any protein in practically any cell line which can be cultured in vitro.

DNA sequences encoding the protein of interest and the processing and/or stabilizing protein(s) may be introduced into the cell on the same vector or on different vectors. It is preferred to use a single vector with one selectable marker in order to minimize problems which can result from marker instability. Genes or cDNAs on a vector may be controlled by separate promoters or by a single promoter. In the latter arrangement, which gives rise to a polycistronic message, the genes or cDNAs will be separated by translational stop and start signals. When transfecting with a large number of DNA sequences, practical limitations on vector size may necessitate the use of two or more vectors, each with its own selectable marker. Two or more vectors may, of course, be used whenever co-expression of a protein of interest and a stabilizing or processing protein is desired.

Other eukaryotic cells, including yeast and filamentous fungi, may also be used within the present invention. These lower eukaryotic hosts provide certain advantages over mammalian cell lines, including ease and economy of culturing and existing industrial fermentation capacity. By manipulating cells as described herein, fungal cells and other eukaryotic cells capable of expressing cloned DNA sequences can be used to produce virtually any protein of interest.

For example, cells of bakers' yeast (Saccharomyces cerevisiae) can be transformed with cloned foreign DNA sequences and cultured to high cell densities, and will express the cloned DNA and secrete the foreign proteins. In some instances, however, the foreign proteins are not secreted or are inactive due to a lack of proper processing or proteolytic degradation. Yeast cells cannot, for instance, gamma-carboxylate proteins or add mammalian-type complex carbohydrate chains to glycoproteins. According to the present invention, this lack of processing can be overcome by transforming yeast host cells with DNA sequences encoding the missing protein(s) (e.g., gamma-carboxylase, glycosylating enzymes). Degradation of foreign proteins may be overcome by transforming the cells to produce protease inhibitors or proteins which bind to the protein of interest. An example of a suitable binding protein is BiP. Binding proteins may also enhance secretion of a foreign protein by altering its conformation. In addition, yeast cells can be transformed to produce foreign proteases, enabling them to produce and secrete active forms of foreign proteins (e.g., mammalian serine proteases) which require specific cleavage for secretion and/or biological activity. Junction points between secretory peptides and mature proteins may be engineered so that cleavage by a co-expressed protease (e.g., thrombin) releases the mature protein.

As noted above, eukaryotic microorganisms, such as the yeast Saccharomvces cerevisiae, or filamentous fungi including Aspergillus species, may also be used as the host cells. particularly preferred species of Aspergillus include A. nidulans, A. niger, A. oryzae, and A. terreus. Techniques for transforming yeast are described, for example, by Beggs (Nature 275:104–108, 1978). Aspergillus species may be transformed according to known procedures, for example, that of Yelton et al. (Proc. Natl. Acad. Sci. USA 81:1740–1747, 1984). Expression vectors for use in yeast include YRp7 (Struhl et al., Proc. Natl. Acad. Sci USA 76:1035–1039, 1979), YEp13 (Broach et al., Gene 8:121–133, 1979), pJDB248 and pJDB219 (Beggs, ibid.), and derivatives thereof. Such vectors will generally comprise a selectable marker, such as the nutritional marker TRP1, which allows selection in a host strain carrying a trp1 mutation, or the pOT1 selectable marker, which permits selection in a tpi⁻ strain grown in rich medium (Kawasaki and Bell, EP 171,142). preferred promoters and terminators for use in yeast expression vectors include those from yeast glycolytic genes (Hitzeman et al., J. Biol. Chem. 255:12073–12080, 1980; Alber and Kawasaki, J. Mol. Appl. Genet, 1:419–434, 1982; Kawasaki, U.S. Pat. No. 4,599, 311) or alcohol dehydrogenase genes (Young et al., in Hollaender et al. (eds.), Genetic Engineering of Microorganisms for Chemicals, Plenum, New York, 1982, p. 335; and Ammerer, Meth. in Enzymology 101:192–201, 1983). To facilitate secretion of a protein of interest produced in a yeast transformant and to obtain proper processing, a signal sequence will generally be provided. Preferably the signal sequence will be obtained from a yeast gene encoding a secreted protein. A particularly preferred signal sequence is the pre-pro region of the MFα1 gene (Kurjan and Herskowitz, Cell 30:933–943, 1982; Kurjan et al., U.S. Pat. No. 4,546,082; and Singh, EP 123,544).

Co-expression of DNA sequences in yeast may be achieved in several ways. It is preferred that the expression unit for the processing or stabilizing protein be integrated into the host cell genome and an isolate which stably produces the processing or stabilizing activity be selected. An expression unit containing the DNA sequence for the protein of interest is then transformed into the host strain. Alternatively, the two expression units may be on different autonomously replicating expression vectors with different selectable markers or on a single expression vector.

In a preferred embodiment, a DNA sequence encoding a foreign processing protein is inserted into a DNA sequence encoding a yeast protein having a similar function. The insertion is designed to substitute the foreign sequence for yeast sequences encoding the processing function(s) of the yeast protein. A particularly preferred such yeast protein is the KEX2 gene product. This protein has been analyzed and its catalytic and other domains have been characterized (Fuller et al., *Yeast Cell Biology*, Cold Spring Harbor Laboratory, Cold Spring Harbor, N.Y., 1987, p. 181). The resulting hybrid sequence, comprising the foreign DNA sequence and yeast sequences encoding transport and cellular localization domains, is then joined to a yeast promoter and terminator. Preferably, the promoter is a strong promoter, such as the TPI1 promoter. This construct may also contain flanking sequences to target the expression unit to a particular integration site in the host cell genome.

Proteins produced according to the present invention may be purified from cell-conditioned media by a variety of procedures known in the art, which may be selected according to the physicochemical characteristics of the particular protein. Suitable methods include affinity chromatography, ion exchange chromatography, gel filtration, high performance liquid chromatography, and combinations of these methods.

Proteins produced according to the present invention may be used within compositions for pharmaceutical, industrial, research and other purposes. For pharmaceutical use, the proteins will generally be combined with a physiologically acceptable carrier or diluent, such as sterile water or sterile saline, and packaged in individual doses in sterile vials. Alternatively, the proteins may be packaged in lyophilized form and reconstituted prior to administration. Administration will generally be by injection or infusion. Pharmaceutical compositions may further contain additional proteins or other compounds of therapeutic value, adjuvants, local anesthetics, etc.

The following examples are offered by way of illustration and not by way of limitation.

EXAMPLES

Except where noted, conventional molecular biology techniques were employed. Restriction endonucleases and other DNA modification enzymes (e.g., T4 polynucleotide kinase, calf alkaline phosphatase, DNA polymerase I [Klenow fragment], T4 polynucleotide ligase) were obtained from Bethesda Research Laboratories, New England Biolabs, or Boehringer-Mannheim and used according to the suppliers' instructions or as described in Maniatis et al. (eds.), *Molecular Cloning: A Laboratory Manual*, Cold Spring Harbor Laboratory, Cold Spring Harbor, N.Y., 1982. Oligonucleotides were synthesized on an Applied Biosystems model 380A DNA synthesizer and purified by polyacrylamide gel electrophoresis on denaturing gels.

Example 1

Production of Tissue Plasminogen Activator

Tissue plasminogen activator (t-PA) cDNAs have been described in the literature. See, for example, Pennica et al. (ibid.), Kaufman et al., (*Mol. Cell. Biol.* 5:1750–1759, 1985), Goeddel et al. (U.S. Pat. No. 4,766,075) and Verheijen et al. (*EMBO J.* 5:3525–3530, 1986). A cDNA clone comprising the coding sequence for mature t-PA was constructed in the inventors' laboratory using as starting material mRNA from the Bowes melanoma cell line (Rijken and Collen, *J. Biol. Chem.* 256:7035–7041, 1981). This cDNA was then used to construct the plasmid pDR1296. *E. coli* strain JM83 transformed with pDR1296 has been deposited with American Type Culture Collection under accession number 53347.

The cDNA in pDR1296 was extended to include the coding sequence for the pre-pro peptide by joining it to a fragment constructed from synthesized oligonucleotides. The synthesized pre-pro fragment was inserted into Bam HI-digested pUC8. Plasmid pIC19R (Marsh et al., *Gene* 32:481–486, 1984) was digested with Sma I and Hind III. The ori region of SV40 from map position 270 (Pvu II) to position 5171 (Hind III) was then ligated to the linearized pIC19R to produce plasmid Zem67. This plasmid was then cleaved with Bgl II and the terminator region from the human growth hormone gene (De Noto et al., *Nuc. Acids Res.* 9:3719–3730, 1981) was inserted as a Bgl II-Bam HI fragment to produce plasmid Zem86. The synthesized t-PA pre-pro sequence was removed from the pUC8 vector by digestion with Bam HI and Xho II. This fragment was inserted into Bgl II-digested Zem86 to produce plasmid Zem88. Plasmid pDR1296 was digested with Bgl II and Bam HI and the t-PA cDNA fragment was isolated and inserted into Bgl II-cut Zem88. The resultant plasmid was designated Zem94.

The vector Zem99, comprising the MT-1 promoter, complete t-PA coding sequence, and the human growth hormone (hGH) terminator, was then assembled as shown in FIG. 1. A Kpn I-Bam HI fragment comprising the MT-1 promoter was isolated from MThGHIII (Palmiter et al., *Science* 222:809–814, 1983) and inserted into pUC18 to construct Zem93. Plasmid EV142, comprising MT-1 and hGH sequences in the pBR322 derivative pBX322 (Palmiter et al., ibid.), was digested with Eco RI, and the fragment comprising the MT-1 promoter and hGH terminator sequences was isolated. This fragment was cloned into Eco RI-digested pUC13 to construct plasmid Zem4. Zem93 was then linearized by digestion with Bam HI and Sal I. Zem4 was digested with Bgl II and Sal I and the hGH terminator was purified. The t-PA pre-pro sequence was removed from the pUC9 vector as a Sau 3A fragment. The three DNA fragments were then joined, and a plasmid having the structure of Zem97 (FIG. 1) was selected. Zem97 was cut with Bgl II and the Bgl II-Bam HI t-PA fragment from pDR1296 was inserted. The resultant vector was designated Zem99.

Figure 2:
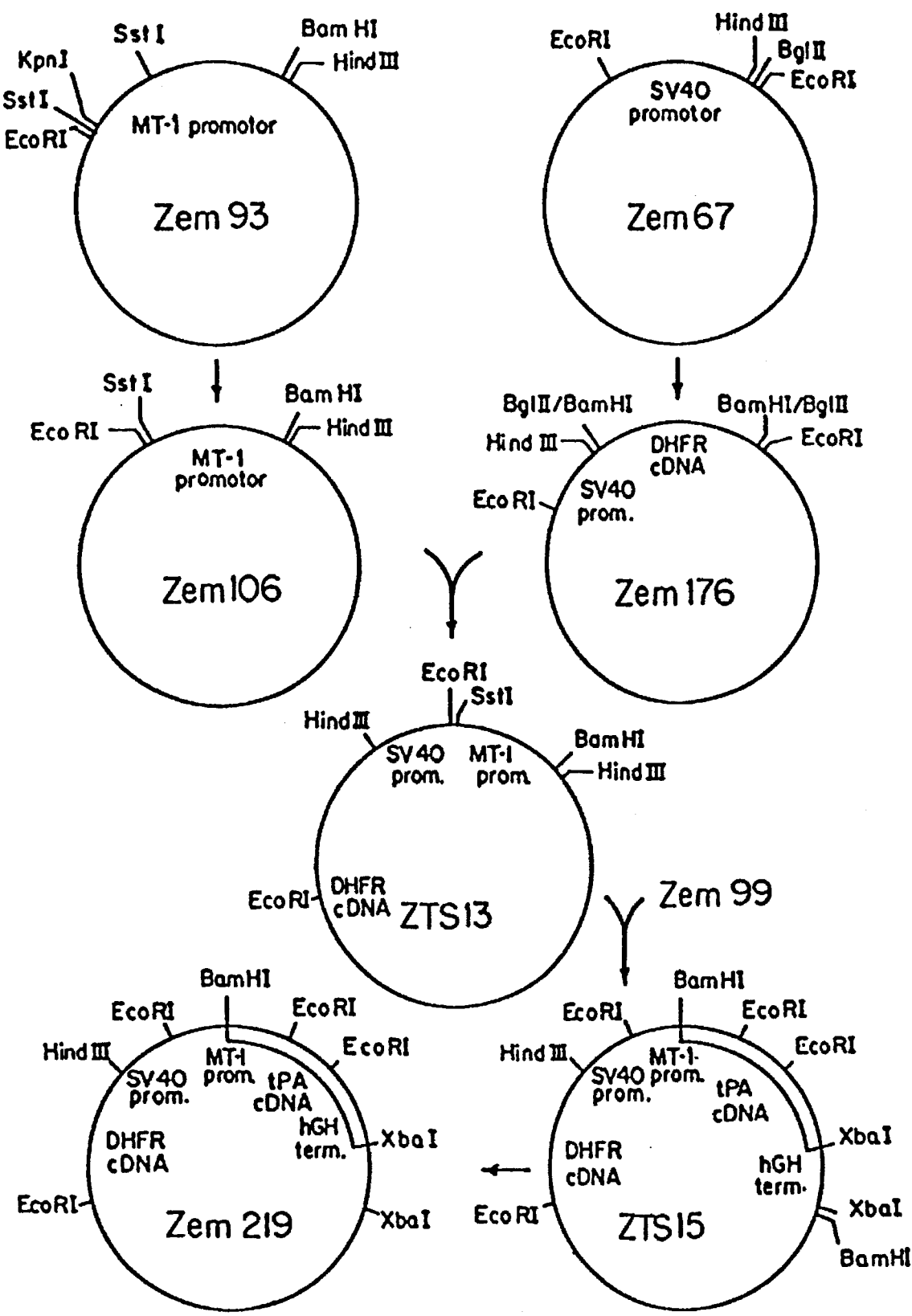
FIG. 2 illustrates the construction of the t-PA expression vector Zem219.

Plasmid pSV2-DHFR (Subramani et al., ibid.) was digested with Cfo I, and the fragment containing the DHFR cDNA and the 3' attached SV40 sequences was isolated, repaired, and ligated to Bam HI linkers. After digestion with Bam HI, an approximately 800 bp fragment containing the entire cDNA and the SV40 terminator region was purified and ligated to Bam HI-digested pUC8. Zem67 was digested with Bgl II and ligated with the Bam HI DHFR-SV40 fragment to generate plasmid Zem176. Plasmid Zem93 was digested with Sst I and re-ligated to generate plasmid Zem106, in which approximately 600 bp of sequence 5' to the MT-1 promoter was eliminated. Plasmid Zem106 was digested with Eco RI and ligated to the Eco RI fragment containing the DHFR gene from plasmid Zem176. The resulting plasmid was designated Zts13. Plasmid Zts13 was digested with Bam HI and ligated to the Bam HI fragment from plasmid Zem99 containing the entire t-PA coding region and hGH terminator sequence. The resulting plasmid was designated Zts15. Zts15 was partially digested with Bam HI, repaired and re-ligated to generate plasmid Zem219, in which the 3' Bam HI site was destroyed (FIG. 2).

Figure 3:
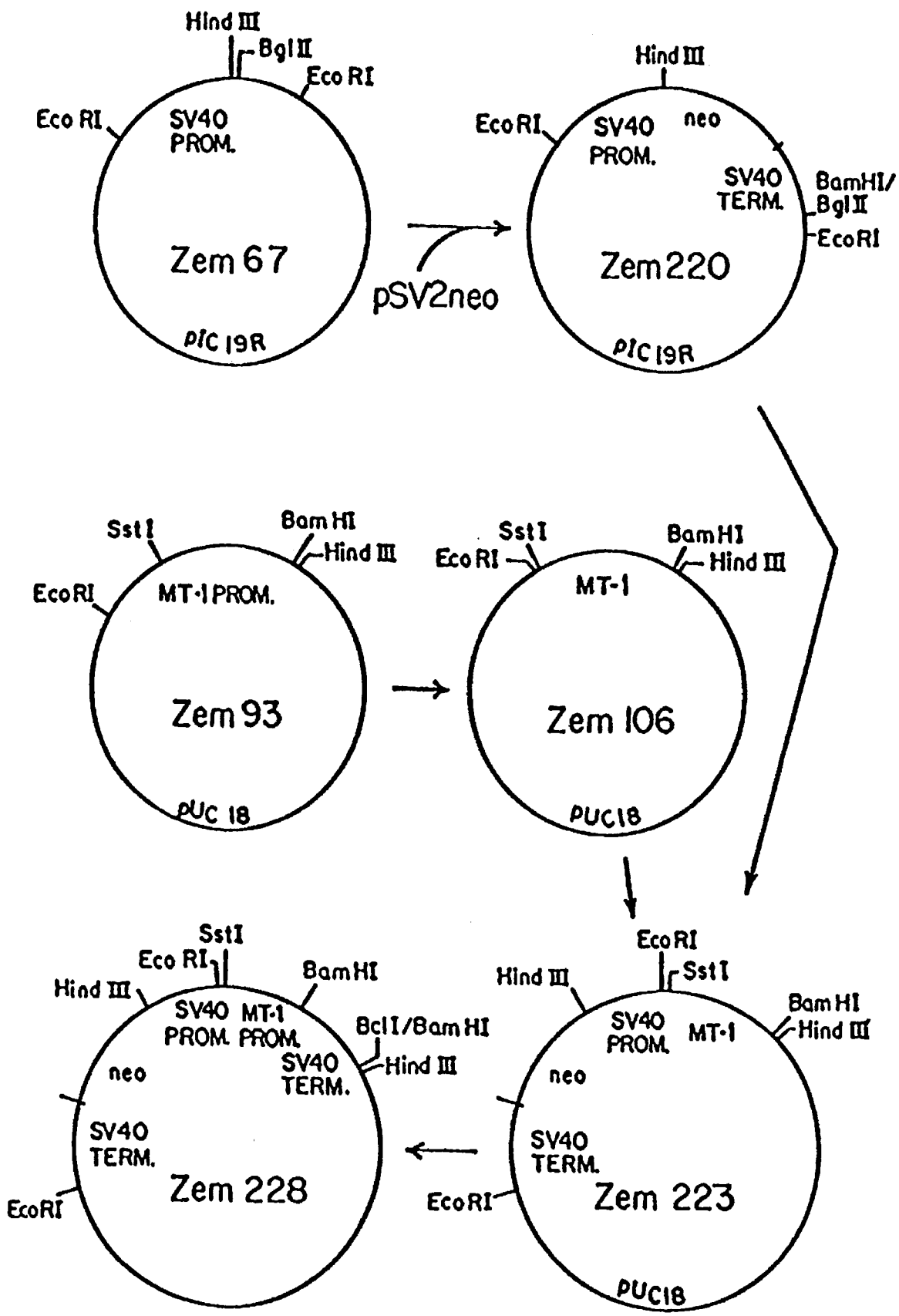
FIG. 3 illustrates the construction of Zem228.

A DNA sequence encoding a protease inhibitor, such as aprotinin, is inserted into a vector carrying the neomycin resistance marker. Zem228 is such a vector. To construct Zem228, Zem67 was digested with Hind III and Bgl II and the Hind III-Bam HI neo+SV40 terminator fragment from pSV2neo (Southern and Berg, *J. Mol. Appl. Genet.* 1:327–341, 1982) was inserted. The resultant vector was designated Zem220. Plasmid Zem93 was digested with Sst I to remove upstream MT-1 sequences and the vector was recircularized to construct Zem106. Zem220 was digested with Eco RI and the fragment containing the expression unit of SV40 promoter-neo-SV40 terminator was recovered and joined to Eco RI-digested Zem106. The resultant vector, designated Zem223, contained the SV40 and MT-1 promoters in opposite orientation. Zem223 was digested with Bam HI and a 237 bp Bcl I-Bam HI SV40 terminator fragment was inserted. The resultant plasmid was designated Zem228 (FIG. 3).

To co-express t-PA and aprotinin, BHK 570 cells are transfected with Zem219 by electroporation. Transfected cells are selected with methotrexate and screened for t-PA production by enzyme-linked immunosorbent assay (ELISA). Cells which are positive for t-PA production are transfected with the Zem228-aprotinin vector and selected with G-418. Selected cells are screened for production of single chain t-PA (e.g., by Western blot) and positive cells are cloned and scaled up for production.

Example 2

Production of Plasminogen

A. Cloning of Alpha-1-Antitrypsin cDNA

A cDNA coding for the predominant form of human α-1-antitrypsin (AAT) was isolated from a human liver cDNA library by conventional procedures using the baboon sequence (Kurachi et al., *Proc. Natl. Acad. Sci. USA* 78:6826–6830, 1980; and Chandra et al., *Biochem. Biophys. Res. Comm.* 103:751–758, 1981) as a DNA hybridization probe as described in U.S. Pat. No. 4,839,283. The library was constructed by inserting human liver cDNA into the Pst I site of the plasmid pBR322 (Bolivar et al., *Gene* 2:95–113, 1977). The AAT cDNA was isolated from the library as a 1500 base pair (bp) Pst I fragment. This fragment was inserted into the Pst I site of pUC13 to produce the plasmid pUCα1. In pUCα1, the AAT sequence is flanked on the 3' end by Xba I and Eco RI sites in the polylinker. This cDNA sequence was used to construct the plasmid pFATPOT, illustrated in FIG. 4. Plasmid pFATPOT has been deposited with the ATCC as a *Saccharomyces cerevisiae* strain E18 transformant, accession number 20699.

Figure 4:
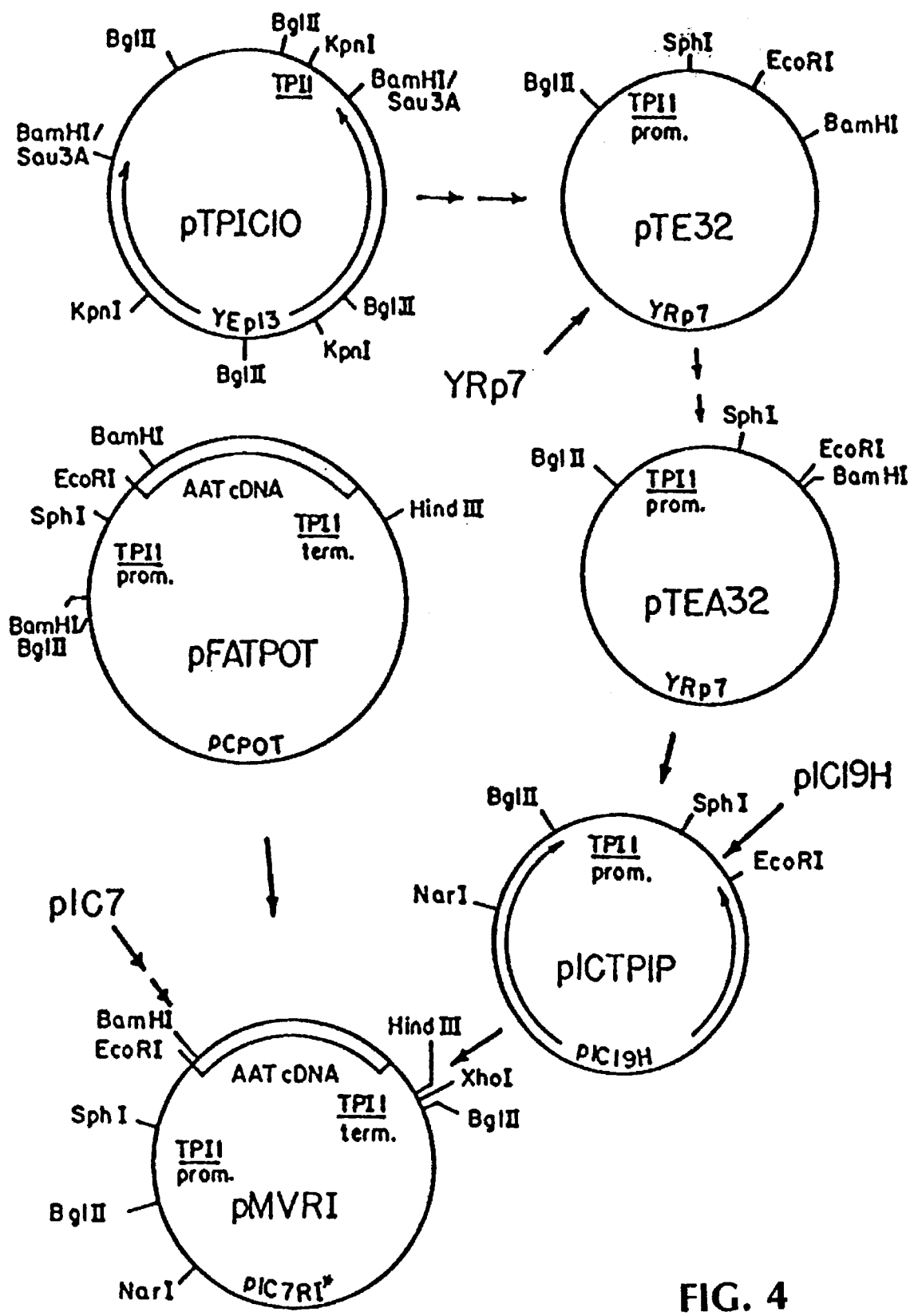
FIG. 4 illustrates the subcloning of an alpha-1-antitrypsin cDNs

The AAT cDNA was then joined to the TPI1 (triose phosphate isomerase gene) terminator in the plasmid pMVR1. This plasmid further comprises the TPI1 promoter and was assembled in the following manner. Plasmid pIC7 (Marsh et al., *Gene* 32:481–486, 1984) was digested with Eco RI, the fragment ends blunted with DNA polymerase I (Klenow fragment), and the linear DNA recircularized using T4 DNA ligase. The resulting plasmid was used to transform *E. coli* RR1. Plasmid DNA was prepared from the transformants and screened for the loss of the Eco RI site. A plasmid having the correct rwas designated pIC was designated pIC7RI\*. The TPI1 promoter fragment was obtained from plasmid pTPIC10 (Alber and Kawasaki, *J. Molec. Appl. Genet.* 1:419–434, 1982) as illustrated in FIG. 4. This plasmid was cut at the unique Kpn I site within the TPI1 gene, the TPI1 coding region was removed with Bal31 exonuclease, and an Eco RI linker (sequence: GGAATTCC) was added to the 3' end of the promoter. Digestion with Bgl II and Eco RI yielded a TPI1 promoter fragment having Bgl II and Eco RI sticky ends. This fragment was then Joined to plasmid YRp7' (Stinchcomb et al., *Nature* 282:39–43, 1979) which had been cut with Bgl II and Eco RI. The resulting plasmid, TE32, was cleaved with Eco RI and Bam HI to remove a portion of the tetracycline resistance gene. The linearized plasmid was then recircularized by the addition of the previously described Eco RI-Bam HI linker to produce plasmid TEA32. Plasmid TEA32 was digested with Bgl II and Eco RI and the ~900 bp partial TPI1 promoter fragment was gel purified. Plasmid pIC19H (Marsh et al., ibid.) was cut with Bgl II and Eco RI and the vector fragment was gel purified. The TPI1 promoter fragment was then ligated to the linearized pIC19H and the mixture was used to transform *E. coli* RR1. Plasmid DNA was prepared and screened for the presence of a ~900 bp Bgl II-Eco RI fragment. A correct plasmid was selected and designated pICTPIP. Plasmid pIC7RI\* was digested with Hind III and Nar I and the 2500 bp fragment was gel purified. The partial TPI1 promoter fragment (ca. 900 bp) was removed from pICTPIP using Nar I and Sph I and was gel purified. pFATPOT was digested with Sph I and Hind III and the 1750 bp fragment comprising a portion of the TPI1 promoter, the AAT cDNA, and the TPI1 terminator was gel purified. The pIC7RI\* fragment, the TPI1 promoter fragment, and the TPI1 promoter-AAT-TPI1 terminator fragment from pFATPOT were then combined in a triple ligation to produce pMVR1 (FIG. 4).

B. Construction of Alpha-1-Antitrypsin Expression Vector and Transfection of BHK Cells For expression and secretion of alpha-1-anti-trypsin by transfected mammalian cells, the Bam HI and Xba I fragment from plasmid pMVR1, containing the entire coding region for AAT from amino acid number 2, was isolated and inserted into Bam HI, Xba I digested Zem219a.

To construct Zem219a, plasmid Zem219 was partially digested with Xba I, repaired and re-ligated to generate plasmid Zem219a, in which the Xba I site 3' to the hGH terminator was destroyed.

Figure 5:
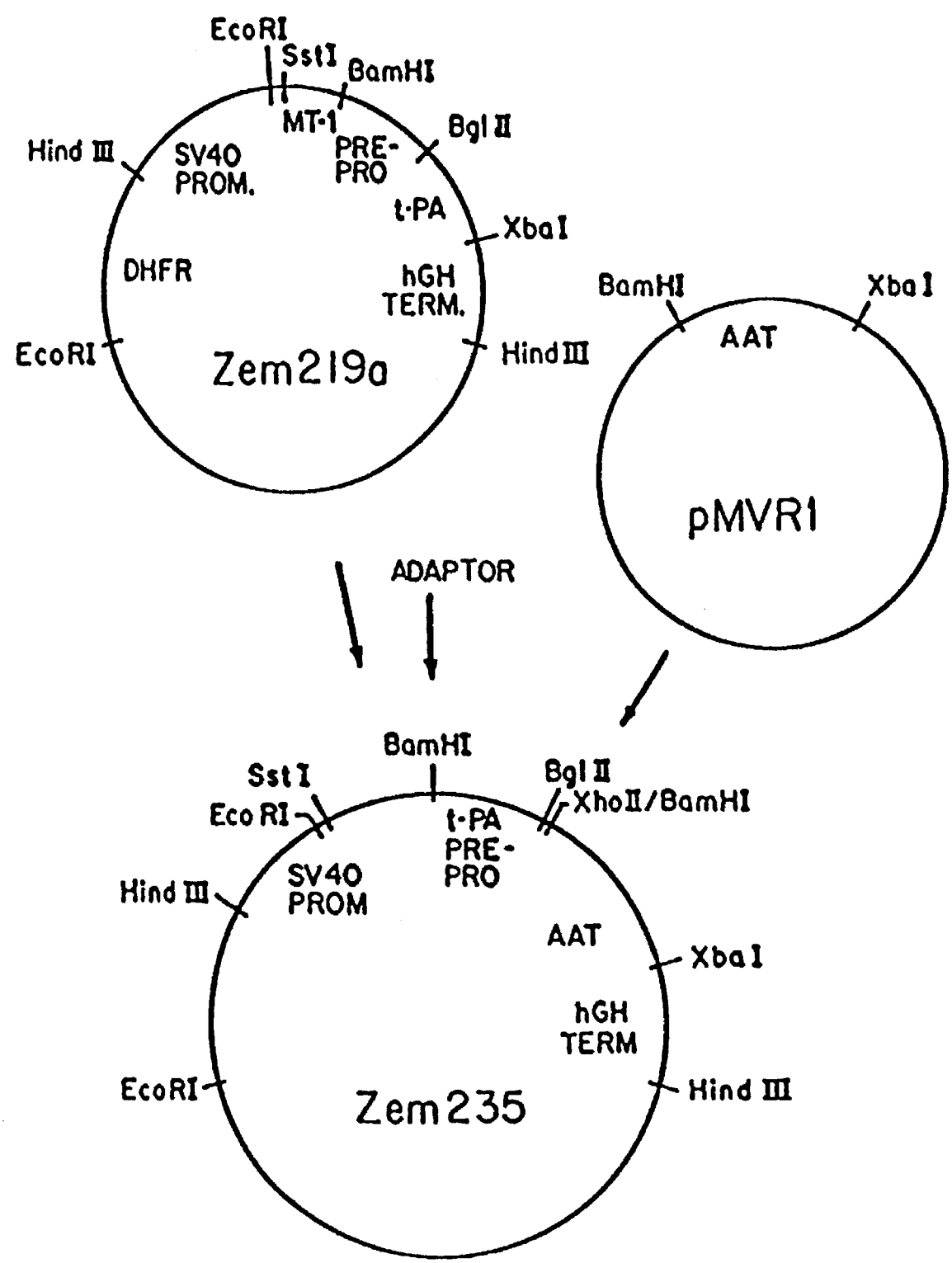
FIG. 5 illustrates the construction of expression vector Zem235.

To construct the AAT expression vector, Zem219a was digested with Bgl II and Xba I and the t-PA coding sequence was removed. Oligonucleotides ZC1173 ($^5$'GAT CTT CA$^3$') and ZC1174 ($^5$'GAT CTG AA$^3$') were annealed to form a Bgl II-Xho II adaptor. The AAT fragment, adaptor and linearized vector were then joined in a three-part ligation to construct Zem235 (FIG. 5). The adaptor correctly aligned the reading frames of the t-PA pre-pro and AAT sequences and restored the glu codon which was missing from the 5' end of the AAT sequence.

Plasmid Zem235 was transfected into BHK 570 cells by electroporation. Methotrexate selection was applied after 48 hours, and after two weeks a number of clones were picked, expanded and characterized for levels of alpha-1-antitrypsin secreted into the culture media. One clone, which secreted AAT at a rate of about 20 μg/ml/day, was selected and designated 235-6.

C. Construction of Plasminogen Expression Vector and Transfection of Cells

A cDNA encoding plasminogen was obtained from Dr. Mark Markson of the University of Washington, Seattle, Wash. The clone had been isolated from a lambda phage library screened with a partial cDNA clone described by Malinowski et al. (ibid.). The sequence of the cDNA is shown in FIG. 6.

Lambda phage DNA was prepared from the positive clone according to conventional procedures. Phage DNA was subjected to a partial Eco RI digestion and an approximately 2800 bp Eco RI fragment containing the entire coding region was recovered and cloned into the Eco RI site of pUC19 to construct plasmid pUC19-Plg.

The 183 bp Bal I-Eco RI fragment containing the 5' end of the coding sequence was isolated from pUC19-Plg and cloned into Sma I, Eco RI digested pUC18 in order to add a Bam HI site to the 5' end. The resultant plasmid was digested with Bam HI and Eco RI and the 190 bp fragment was isolated.

Plasmid pUC19-Plg was digested with Eco RI and Eco RV and the fragment containing the middle region of the cDNA was isolated.

To obtain the 3' portion of the plasminogen cDNA, the eDNA was subcloned into pUC119 and mutagenized to contain a Kpn I site at codons 542–543. The Kpn I-Sph I 3' plasminogen fragment was then joined, via an oligonucleotide linker, to a Bam HI-Sca I 5' t-PA cDNA fragment in pUC118. The resulting plasmid was digested with Eco RV and Xba I, and the ~660 bp 3' plasminogen fragment was isolated.

The three plasminogen cDNA fragments (Bam HI-Eco RI, Eco RI-Eco RV and Eco RV-Xba I) were combined with Bam HI, Xba I digested Zem219b for ligation to generate plasmid 219b-Plg. (Zem219b was derived from Zem219a by digesting that vector with Bam HI and Xba I, removing the t-PA cDNA sequences, and ligating the vector fragment with a Bam HI-Xba I adaptor.) The Bam HI plasminogen fragment was then removed from the Zem219b vector and inserted into Bam HI-digested Zem228. The Zem228-derived plasminogen expression vector was designated Zem228-Plg.

Zem228-Plg was transfected into the AAT-expressing 235-6 cell line by the electroporation procedure, essentially as described by Neumann (ibid.). Colonies were selected and assayed for plasminogen production by enzyme-linked immunosorbent assay (ELISA). The assay used a goat polyclonal antiserum to human plasminogen (American Diagnostica) as the capture antibody. Immunoreactive material was detected by means of biotinylated rabbit polyclonal antibody against human plasminogen and avidin-conjugated horseradish peroxidase.

Ten positive clones were put into six-well tissue culture dishes. When the cells were 80%–90% confluent, they were put into cysteine-deficient medium for one hour. Fifty microcuries of $^{35}S$-cysteine was added to each well (1 ml culture volume/well) and the cells were incubated overnight and the media were harvested for assay.

The cells were washed with cold PBS and an extract was prepared to assay for cytoplasmic plasminogen. The cells were suspended in 1 ml RIP A buffer (10 mM Tris pH 7.4, 1% deoxycholate, 1% Triton X-100, 0.1% SDS, 5 mM EDTA, 0.7M NaCl). The lysates were freeze-thawed two times on dry ice and centrifuged in the cold for 15 minutes at 10,000 rpm. The supernatants were then used for radioimmune precipitation.

Media and cell extract samples were assayed for plasminogen by radioimmune precipitation. Samples (in a volume of 0.1 to 1.0 ml) were combined with 5–10 µl of preimmune serum, incubated on ice for 1 hour and then mixed with 50–100 µl of Staphylococcus aureus (Pansorbin, Sigma Chemical Co., St. Louis, Mo.) and incubated for 1 hour on ice. After centrifugation, the supernatants were mixed with 5 µl of rabbit polyclonal antiserum to human plasminogen (Boehringer-Mannheim) and incubated on ice for one hour. Fifty µl of Staphylococcus aureus was added and the mixture was incubated one hour on ice. The cells were pelleted and the pellets were washed with on ml PBS containing 0.5% NP-40, 0.1% SDS. The washed cells were pelleted, resuspended in 50 µl PBS plus 50 µl 2× loading buffer (0.1M Tris pH 6.8, 16% glycerol 3.2% SDS, 8% β-mercaptoethanol, 0.002% bromphenol blue), boiled 5 minutes and electrophoresed on a 10% polyacrylamide gel. Proteins were visualized by silver staining and autoradiography.

Figure 7A:
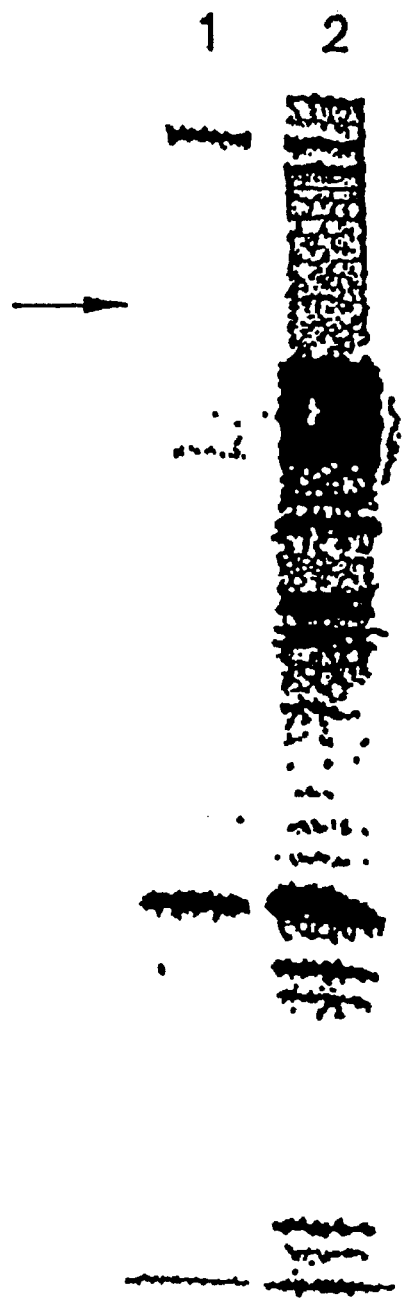
FIG. 7 illustrates the production of plasminogen in transfected BHK cells (a), and in transfected BHK cells co-expressing wild-type alpha-1-antitrypsin (b). Lanes 1—media samples; lanes 2—cytoplasmic extracts. Arrows indicate the position of intact plasminogen (92 kd).
Figure 7B:
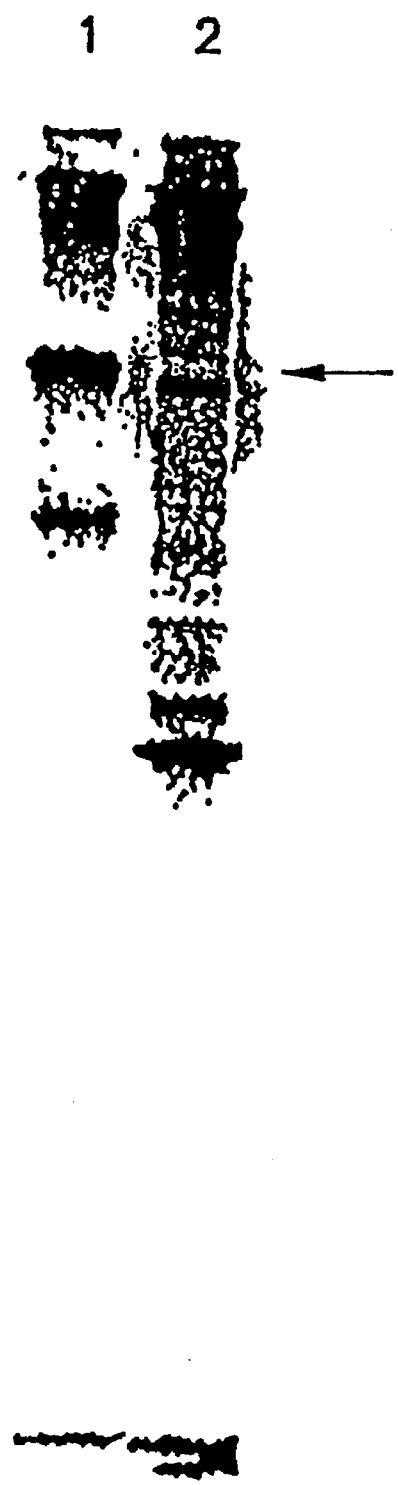

Assay results showed that AAT-producing cells secreted full-length plasminogen into the culture media. In contrast, control BHK cells (i.e., cells transfected with 219b-Plg but not Zem 235) did not secrete detectable amounts of plasminogen and contained degraded plasminogen in the cytoplasm (FIG. 7).

D. Co-expression of Plasminogen and Arg (358) Alpha-1-Antitrypsin

A DNA sequence encoding Arg (358) AAT was constructed using conventional techniques of site-specific mutagenesis as described by Insley et al. (U.S. Pat. No. 4,711,848). This DNA sequence (Bam HI-Xba I fragment) was inserted into pUC13 to construct plasmid pUZC136.

A mammalian cell expression vector for Arg (358) AAT was then constructed. Plasmid Zem235 (FIG. 5) was digested with Bam HI and Eco RV, and the fragment comprising the t-PA pre-pro sequence and the 5' portion of the AAT cDNA was recovered. Plasmid pUZC136 was digested with Eco RV and Xba I, and the 3' Arg (358) AAT fragment was recovered. The two fragments were then joined to Bam HI, Xba I cut Zem219b. The resulting plasmid was designated Zem256. The presence of the correct construction was verified by Southern blotting of Zem256 and Zem235 (control) using the mutagenic oligonucleotide (5' ATA CCC AGG TCT ATC CCC 3') as a probe.

Plasmids Zem256 and Zem228-Plg were transfected into BHK 570 cells by the calcium phosphate coprecipitation method. Transfected cells were selected in Dulbecco's modified Eagle's medium (DMEM) supplemented with 5% fetal bovine serum (obtained from HyClone Laboratories, Logan, Utah, and heat inactivated for 30 minutes at 56° C. followed by passage through a lysine-Sepharose column [Pharmacia, Piscataway, N.J.]), 2 mM L-glutamine, 1× penicillin-streptomycin-neomycin antibiotic mix (PSN; obtained from Gibco, Grand Island, N.Y.), 500 µg/ml G-418 (Gibco) and methotrexate (1 µM or 10 µM) at 37° C. in a 5% $CO_2$ atmosphere. Stable transfectants were clonally selected by culturing under the same conditions.

Figure 8:
FIG. 8 illustrates the production of plasminogen in BHK cells co-expressing Arg (358) alpha-1-antitrypsin (lane 1) and in control cells co-expressing wild-type alpha-1-antitrypsin (lane 2). The arrow indicates the position of intact plasminogen.

The cultured cells were transferred to serum-free medium (50% DMEM, 50% Ham's F12, 1 mM sodium pyruvate, 2 mM L-glutamine, 1× PSN antibiotic mix, 5 mg/l insulin, 3 µg/l selenium, 10 mg/l fetuin, 20 mg/l transferrin and 25 mM pH 7.2 HEPES buffer) and cultured at 37° C. in 5% $CO_2$. Media samples were analyzed by radioimmune precipitation, gel electrophoresis and autoradiography. FIG. 8 compares gel electrophoresis patterns of plasminogen produced by BHK cells co-expressing Arg (358) AAT (lane 1) and wild-type AAT (lane 2). The data indicate that BHK cells co-expressing the Arg (358) variant of AAT produce significantly greater quantities of intact glu-plasminogen than BHK cells co-expressing wild-type AAT.

E. Co-expression of Plasminogen and Plasminogen Activator Inhibitor 1

Figure 9:
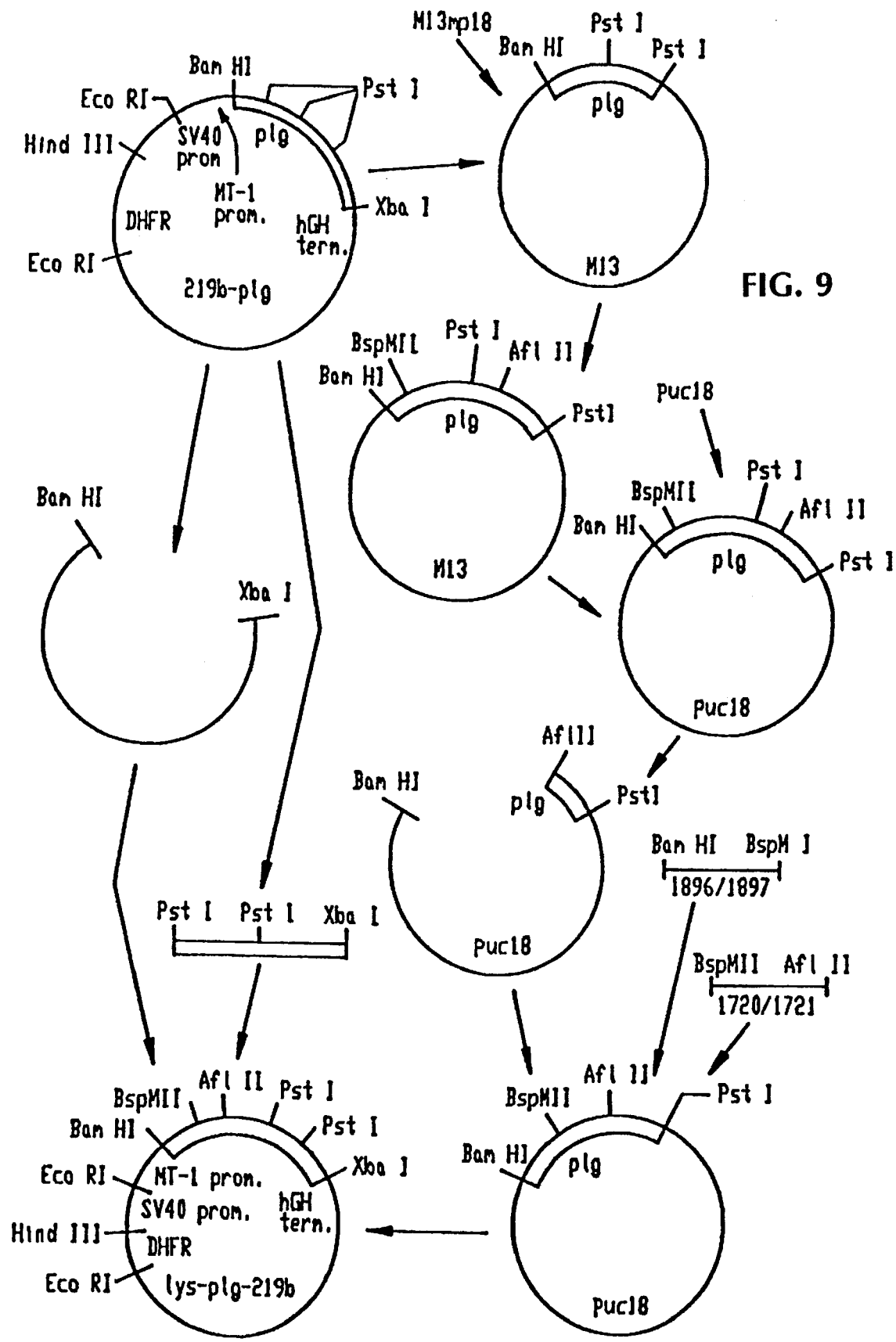
FIG. 9 illustrates the construction of an expression vector for lys-plasminogen.

An expression vector for lys-plasminogen was constructed as shown in FIG. 9. Plasmid 219b-plg was partially digested with Pst I and digested to completion with Bam HI. The 5' plasminogen fragment was recovered and inserted into M13mp18. Afl II and Bsm MII sites were introduced into the plasminogen sequence by site-specific mutagenesis in a single step using the mutagenic oligonucleotides ZC1726 (5' TTG AAA AGA AAG TGT ACT TAA GTG AGT GCA AGA CTG 3') (for introduction of the Afl II site) and ZC1727 (5' TTC TGA AAT CCG GAC AAG GAG AG 3') (Bsp MII site). The mutagenized plasminogen sequence was then isolated as a Bam HI-Pst I fragment and inserted into pUC18. The resulting plasmid was digested to completion with Afl II, and the 3.2 kb linearized plasmid was gel purified. The isolated DNA then was digested to completion with Bam HI, and the fragment comprising the pUC sequences and 3'-most portion of the plasminogen fragment was gel purified. The 5'-most coding sequence for lys-plasminogen was constructed from synthesized oligonucleotides. Oligonucleotides ZC1720 (5' TTA AGT ACA CTT TTC CTT GT 3') and ZC1721 (5' CCG GAC AAG GAA AAG TGT AC 3') were annealed. Oligonucleotides ZC1896 (5' GAT CCA CCA TGG AAC ATA AGG AAG TGG TTC TTC TAC TTC TTT TAT TTC TGA AAT 3') and ZC1897 (5' CCG GAT TTC AGA AAT AAA AGA AGT AGA AGA ACC ACT TCC TTA TGT TCC ATG GTG 3') were annealed. The annealed oligonucleotide pairs and the Bam HI-Afl II pUC18+plasminogen fragment were then joined in a three-part ligation. The resulting plasmid was digested with Bam HI and Pst I, and the fragment comprising the coding sequence for the amino terminus of lys-plasminogen was gel purified. The final expression vector was constructed by ligating the Bam HI-Xba I vector fragment from 219b-Plg, the Pst I-Xba I 3' plasminogen coding sequence, and the Bam HI-Pst I 5' lys-plasminogen sequence. This vector was designated lys-plg-219b.

A cDNA encoding plasminogen activator inhibitor 1 (PAI-1) was obtained from a cDNA library prepared from an SV40-transformed human fibroblast cell line as described by Andreasen et al. (ibid.). A Bam HI-Bgl II fragment containing the coding sequence for the entire protein was inserted into Bam HI, Bgl II-digested Zem229. (Zem229 is similar to Zem228 but contains a DHFR gene as a selectable marker instead of the neomycin resistance gene; see FIG. 13.) The resulting expression vector was designated Zem261. A similar Zem228-derived vector was designated Zem260.

The vectors 219b-Plg and Zem261 were cotransfected into BHK 570 cells by the calcium phosphate method. Transfectants were selected in serum-containing media with 1 µM methotrexate and cultured essentially as described above in serum-containing media.

In a similar manner, the lys-plasminogen expression vector lys-plg-219b and Zem261 were cotransfected into BHK 570 cells, and transfectants were selected.

Figure 10:
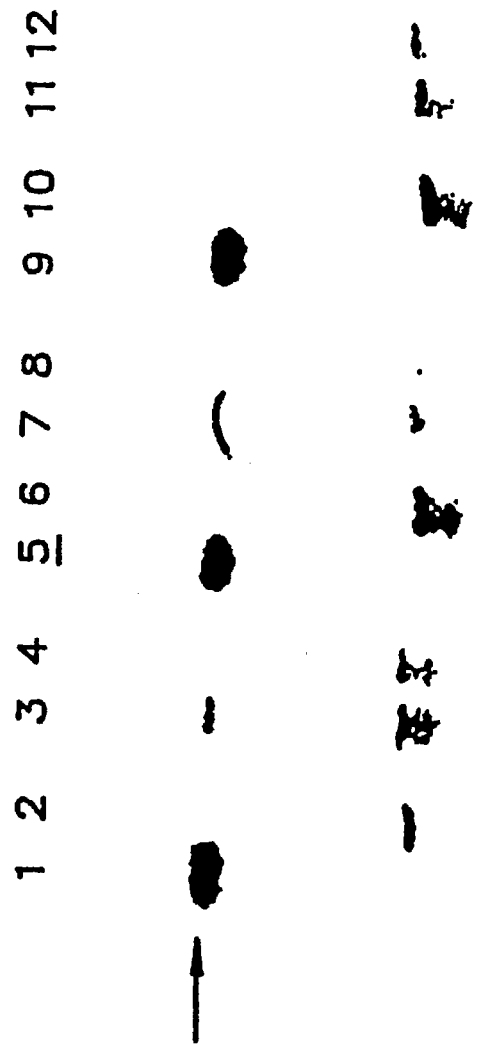
FIG. 10 illustrates the results of radioimmune precipitations on three BHK cell isolates co-expressing glu-plasminogen and plasminogen activator inhibitor 1 (PAI-1). Odd-numbered lanes show samples assayed with antisera to plasminogen. Even-numbered lanes were assayed with antisera to PAI-1. Lanes 1, 2, 5, 6, 9, and 10 are conditioned media samples. Lanes 3, 4, 7, 8, 11, and 12 are cell extracts. The arrow indicates the position of full-length glu-plasminogen.

Secreted proteins and cell extracts were assayed for the presence of plasminogen and PAI-1 by radioimmune precipitation using either rabbit antisera to human plasminogen (Boehringer-Mannheim) or antisera to rat PAI-1 (American Diagnostica). Co-expression of both lys-plasminogen and glu-plasminogen with PAI-1 yielded full-length plasminogen proteins. An autoradiogram showing the results of a representative experiment is shown in FIG. 10. As can be seen from this experiment, three isolates of BHK cells (ATCC CRL 1632) co-expressing glu-plasminogen and PAI-1 secreted full-length glu-plasminogen (arrow) and PAI-1.

F. Co-expression of Lys-Plasminogen and Alpha-2 Plasmin Inhibitor

A full-length $\alpha_2$-PI clone (2.2–2.3 kb) was obtained from a λgt11 cDNA library made with mRNA from HepG2 cells. The library was probed with an oligonucleotide corresponding to the sequence encoding the amino terminus of $\alpha_2$-PI from nucleotide number 25 (5' GAA CAC GGA GCA GGG GCC TTG CAG GCA GGA CCA 3'). The $\alpha_2$-PI cDNA was isolated from a partial Eco RI digest of a plaque-purified positive λgt11 clone. The 2.2–2.3 kb fragment was purified by low melting temperature agarose gel electrophoresis. Plasmid pIC19H was cut with Eco RI and treated with calf intestinal phosphatase, and the vector and the $\alpha_2$-PI Eco RI partial fragment were ligated together and used to transform E. coli DH5α cells by electrotransformation using a pulse of 2 KVolts/cm over a 10-millisecond period. Orientation of the α$\alpha_2$-PI insert was established by restriction mapping using Eco RI or Hind III. A plasmid having the 5' end of the $\alpha_2$-PI insert adjacent to the Bgl II site in the vector was selected and designated pPAB4.

The $\alpha_2$-PI fragment (2.1–2.2 kb) was isolated from a Bam HI+Bgl II digest of pPAB4 using low melting temperature agarose gel electrophoresis. The Bam HI/Bgl II $\alpha_2$-PI fragment and Bam HI digested and phosphatased Zem228 were ligated and used to transform E. coli DH5α cells as described above. Clones were grown up overnight at 37° C. on LB/Amp (50 µg/ml) agarose plates. Random clones were selected and tested for the presence of plasmid with insert. Orientation of the $\alpha_2$-PI insert in positive clones was established by restriction mapping using Eco RI or Mind III. A plasmid having the $\alpha_2$-PI insert in the correct orientation relative to the MT-1 promoter and SV40 terminator was chosen and designated pPAB5.

Two uncut cesium chloride banded plasmids were introduced into tk⁻ts13 BHK cells (ATCC CRL 1632) by the calcium phosphate transfection procedure. The BHK cells were cultured to a final density of 7–8×10$^5$ cells/ml prior to transfection in a 10 cm petri dish in standard growth media (DMEM supplemented with 10% fetal bovine serum, 1% PSN, 2 mM L-glutamine, and 1 mM sodium pyruvate). 10 µg each of plasmids pPAB5 and lys-plg-219b were coprecipitated in 0.5 ml of 2× Hebs (containing, per 100 ml, 1 g Hepes, 1.6 g NaCl, 0.7 g KCl, 0.3 g Na$_2$HPO$_4$.2H$_2$O, 0.2 g dextrose, pH adjusted to 7.05 with 1N NaOH) while bubbling in 0.25M calcium chloride. The precipitant was applied to the cultured cells, which were then incubated for 3–4 hours at 37° C. in a CO$_2$ incubator. Cells were aspirated, then treated with 20% glycerol/Tris Saline (containing, per liter, 0.375 g KCl, 0.71 g Na$_2$HPO$_4$.2H$_2$O, 8.1 g NaCl, 3 g Tris-HCl, 0.5 g sucrose, pH adjusted to 7.9 with 10N NaOH) for 2–5 minutes at room temperature, washed two times with Tris/Saline, and fed with 10 ml of standard growth media. Two days after transfection, the cells were put under selective growth conditions (500 µg/ml G418 and 250 nM or 1 µM MTX in standard growth media). The media was changed every 3–5 days. After 10–21 days, the transfected cells were screened by immunofilter assay for co-expression of $\alpha_2$-PI and lysplasminogen. Clones which were positive for $\alpha_2$-PI and lys-plasminogen expression were picked and amplified by sequential fivefold increases in MTX concentrations.

The vectors lys-plg-219b and pPAB5 were cotransfected into BHK 570 cells by the calcium phosphate method. Cells were cultured in standard growth media containing 500 µg/ml G418 and 1 µM or 10 µM MTX. Transfectants identified as positive for plasminogen expression by immunofilter assay were further characterized by ELISA and radioimmune precipitation. The cells were found to produce full-length lys-plasminogen at about 5 μg/ml.

Example 3

Production of Protein C

A. protein C cDNA Cloning

A cDNA coding for a portion of human protein C was prepared as described by Foster and Davie (ibid.). Briefly, a λgt11 cDNA library was prepared from human liver mRNA by conventional methods. Clones were screened using $^{125}$I-labeled affinity-purified antibody to human protein C, and phage were prepared from positive clones by the plate lysate method (Maniatis et al., ibid.), followed by banding on a cesium chloride gradient. The cDNA inserts were removed using Eco RI and subcloned into the plasmid pUC9 (Vieira and Messing, *Gene* 19:259–268, 1982). Restriction fragments were subcloned in the phage vectors M13mp10 and M13mp11 (Messing, *Meth. in Enzymology* 101:20–77, 1983) and sequenced by the dideoxy method (Sanger et al., *Proc. Natl. Acad. Sci. USA* 74:5463–5467, 1977). A clone was selected which contained DNA corresponding to the known partial sequence of human protein C (Kisiel, ibid.) and encoded protein C beginning at amino acid 64 of the light chain and extending through the heavy chain and into the 3' noncoding region. This clone was designated λHC1375. A second cDNA clone coding for protein C from amino acid 24 was also identified. The insert from this clone was subcloned into pUC9 and the resulting plasmid was designated pHCλ6L. This clone encodes a major portion of protein C, including the heavy chain coding region, termination codon, and 3' noncoding region.

The cDNA insert from λHC1375 was nick translated using α-$^{32}$p dNTP's, and used to probe a human genomic library in phage λCharon 4A (Maniatis et al., *Cell* 15:687–702, 1978) using the plaque hybridization procedure of Benton and David (*Science* 196:181–182, 1977) as modified by Woo (*Meth. in Enzymology* 68:381–395, 1979). Positive clones were isolated and plaque-purified (Foster et al., *Proc. Natl. Acad. Sci. USA* 82:4673–4677, 1985, herein incorporated by reference). Phage DNA prepared from positive clones (Silhavy et al., in *Experiments with Gene Fusion*, Cold Spring Harbor Laboratory, 1984) was digested with Eco RI or Bgl II, and the genomic inserts were purified and subcloned in pUC9. Insert restriction fragments were subcloned into M13 vectors and sequenced to confirm their identity and establish the DNA sequence of the entire gene.

A genomic fragment containing an exon corresponding to amino acids -42 to -19 of the pre-pro peptide of protein C was isolated, nick translated, and used as a probe to screen a cDNA library constructed by the technique of Gubler and Hoffman (*Gene* 25:263–269, 1983) using mRNA from HEPG2 cells. This cell line was derived from human hepatocytes and was previously shown to synthesize protein C (Fair and Bahnak, *Blood* 64:194–204, 1984). Ten positive clones comprising cDNA inserted into the Eco RI site of phage λgt11 were isolated and screened with an oligonucleotide probe corresponding to the 5' noncoding region of the protein C gene. One clone was also positive with this probe and its entire nucleotide sequence was determined. The cDNA contained 70 bp of 5' untranslated sequence, the entire coding sequence for human prepro-protein C, and the entire 3' noncoding region corresponding to the second polyadenylation site.

B. Construction of Vector pD5

Figure 11:
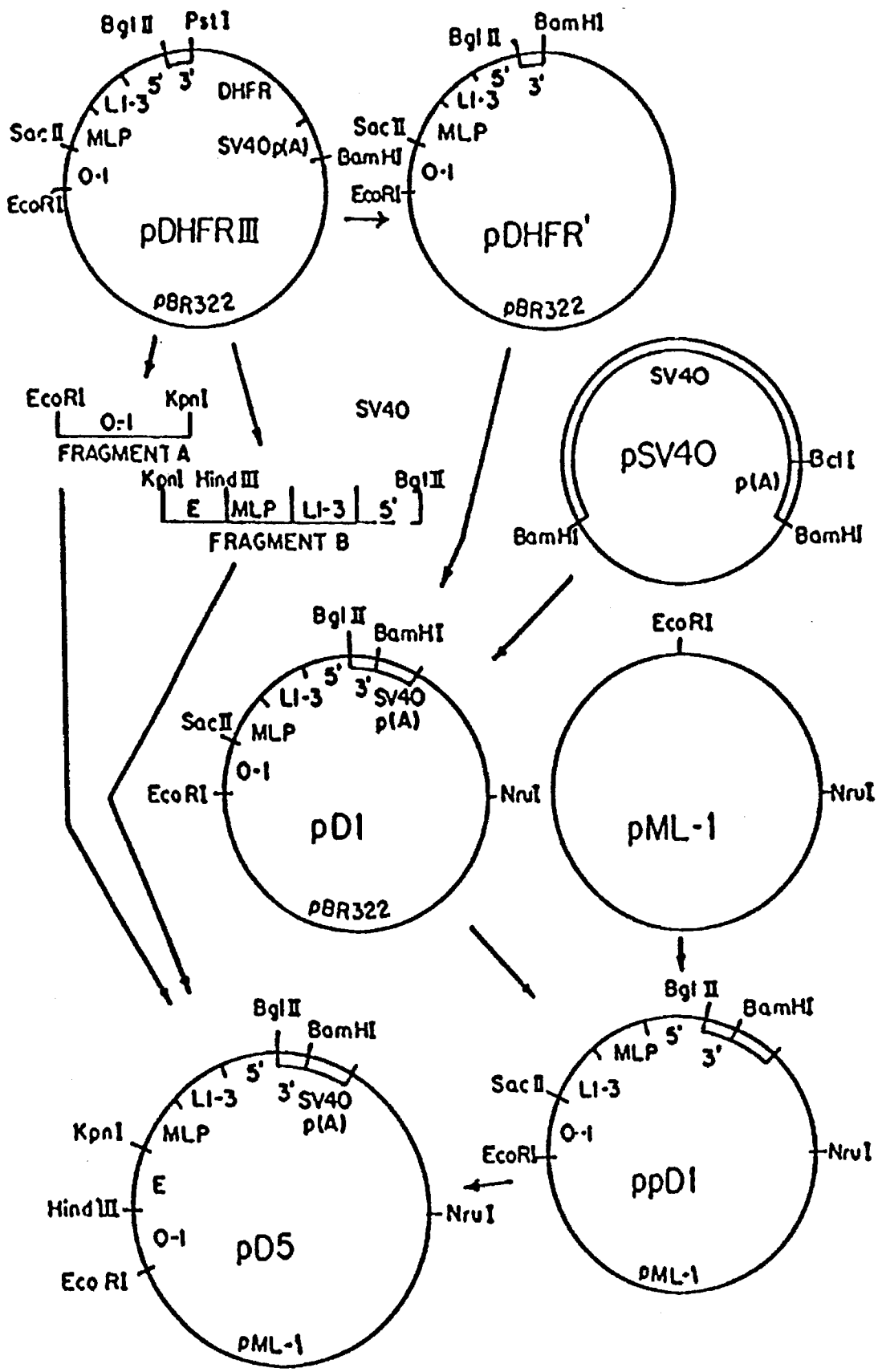
FIG. 11 illustrates the construction of the vector pD5. Symbols used are: 0-1, the adenovirus 5 0-1 map unit sequence; E, the SV40 enhancer; MLP, the adenovirus 2 major late promoter; L1-3, the adenovirus 2 tripartite leader; 5',5' splice site; 3',3' splice site; p(A), polyadenylation signal; DHFR, dihydrofolate reductase gene.

The vector pD5 was derived from pDHFRIII as shown in FIG. 11. The Pst I site immediately upstream from the DHFR sequence in pDHFRIII (Berkner and Sharp, *Nuc. Acids Res.* 13:841–857, 1985) was converted to a Bam HI site by digesting 10 μg of plasmid with 5 units of Pst I for 10 minutes at 37° C. in 100 μl buffer A (10 mM Tris pH 8, 10 mM MgCl$_2$, 6 mM NaCl, 7 mM β-MSH). The DNA was phenol extracted, EtOH precipitated, and resuspended in 40 μl buffer B (50 mM Tris pH 8, 7 mM MgCl$_2$, 7 mM β-MSH) containing 10 mM dCTP and 16 units T$_4$ DNA polymerase and incubated at 12° C. for 60 minutes. Following EtOH precipitation, the DNA was ligated to 2.5 μg kinased Bam HI linkers in 14 μl buffer C (10 mM Tris pH 8, 10 mM MgCl$_2$, 1 mM DTT, 1.4 mM ATP) containing 400 units T$_4$ polynucleotide ligase for 12 hours at 12° C. Following phenol extraction and EtOH precipitation, the DNA was resuspended in 120 μl buffer D (75 mM KCl, 6 mM Tris pH 7.5, 10 mM MgCl$_2$, 1 mM DDT), digested with 100 units Bam HI for 60 minutes at 50° C., then electrophoresed through agarose. The 4.9 kb DNA fragment containing pBR322 and vector sequences (10 μg) was isolated from the gel, ligated in 10 μl buffer C containing 50 units T$_4$ polynucleotide ligase for 2 hours at 12° C., and used to transform *E. coli* HB101. Positive colonies were identified by rapid DNA preparation analysis, and plasmid DNA (designated pDHFR') was prepared.

Plasmid pD1 was then generated by first cleaving 25 μg of pSV40 (comprising Bam HI-digested SV40 DNA cloned into the Bam HI site of pML-1 [Lusky and Botchan, *Nature* 293:79–81, 1981]) in 100 μl buffer D with 25 units Bcl I for 60 minutes at 50° C., followed by the addition of 50 units of Bam HI and additional incubation at 37° C. for 60 minutes. Plasmid pDHFR' was linearized with Bam HI and treated with calf intestinal phosphatase. DNA fragments were resolved by agarose gel electrophoresis, and the 4.9 kb pDHFR' fragment and 0.2 kb SV40 fragment were isolated. These fragments (200 ng pDHFR' DNA and 100 ng SV40 DNA) were incubated in 10 μl buffer C containing 100 units T$_4$ polynucleotide ligase for 4 hours at 12° C., and the resulting construct (pD1) was used to transform *E. coli* RR1.

As shown in FIG. 11, plasmid pD1 was modified by deleting the "poison" sequences in the pBR322 region (Lusky and Botchan, ibid.). Plasmids pD1 (6.6 μg) and pML-1 (4 μg) were incubated in 50 μl buffer A with 10 units each Eco RI and Nru I for 2 hours at 37° C., followed by agarose gel electrophoresis. The 1.7 kb pD1 fragment and 1.8 kb pML-1 fragment were isolated and ligated together (50 ng each) in 20 μl buffer C containing 100 units T$_4$ polynucleotide ligase for 2 hours at 12° C., followed by transformation into *E. coli* HB101. Colonies containing the desired construct (designated ppD1) were identified by rapid preparation analysis. Ten μg of ppD1 was then digested with 20 units each Eco RI and Bgl II, in 50 μl buffer A for 2 hours at 37° C. The DNA was electrophoresed through agarose, and the desired 2.8 kb fragment (fragment C) comprising the pML-1, 3' splice site and poly A sequences was isolated.

To generate the remaining fragments used in constructing pD5, pDHFRIII was modified to convert the Sac II (Sst II) site into either a Hind III or Kpn I site. Ten μg pDHFRIII were digested with 20 units Sst III for 2 hours at 37° C., followed by phenol extraction and ethanol precipitation. Resuspended DNA was incubated in 100 μl buffer B containing 10 mM dCTP and 16 units T$_4$ DNA polymerase for 60 minutes at 12° C., phenol extracted, dialyzed, and ethanol precipitated. DNA (5 μg) was ligated with 50 ng kinased Hind III or Kpn I linkers in 20 μl buffer C containing 400 units T$_4$ DNA ligase for 10 hours at 12° C., phenol extracted, and ethanol precipitated. After resuspension in 50 μl buffer A, the resultant plasmids were digested with 50 units Hind III or Kpn I, as appropriate, and electrophoresed through agarose. Gelisolated DNA (250 ng) was ligated in 30 μl buffer C containing 400 units T$_4$ DNA ligase for 4 hours at 12° C. and used to transform *E. coli* RR1. The resultant plasmids were designated pDHFRIII (Hind III) and pDH- FRIII (Kpn I). A 0.4 kb Eco RI-Kpn I fragment (fragment A) was then purified from pDHFRIII (Kpn I) by digestion with Eco RI and Kpn I followed by agarose gel electrophoresis.

The SV40 enhancer sequence was inserted into pDHFRIII (Hind III) as follows: 50 μg SV40 DNA was incubated in 120 μl buffer A with 50 units Hind III for 2 hours at 37° C., and the Hind III C SV40 fragment (5171–1046 bp) was gel purified. Plasmid pDHFRIII (Hind III) (10 μg) was treated with 250 ng calf intestinal phsophatase for 1 hour at 37° C., phenol extracted and ethanol precipitated. The linearized plasmid (50 ng) was ligated with 250 ng Hind III C SV40 fragment in 16 μl buffer C for 3 hours at 12° C., using 200 units T$_4$ polynucleotide ligase, and transformed into *E. coli* HB101. A 0.9 kb Kpn I-Bgl II fragment (fragment B) was then isolated from this plasmid.

For the final construction of pD5, fragments A and B (50 ng each) were ligated with 10 ng fragment C with 200 units T$_4$ polynucleotide ligase for 4 hours at 12° C., followed by transfection of *E. coli* RR1. Positive colonies were detected by rapid preparation analysis, and a large-scale preparation of pD5 (FIG. 11) was made.

C. Construction of Expression Vector p594

The expression of protein C cDNA was achieved in the vector pDX. This vector was derived from pD11 and pD5'. Plasmid pD5' is identical to pD5 except that the SV40 polyadenylation signal (i.e., the SV40 Bam HI [2533 bp] to Bcl I [2770 bp] fragment) is in the late orientation. Thus, pD5' contains a Bam HI site as the site of gene insertion. Plasmid pD11 differs from pD5 in that the Hind III (5171 bp in the SV40 genome) to Kpn I (294 bp in SV40) fragment, containing enhancer sequences, is in the opposite orientation.

Figure 12:
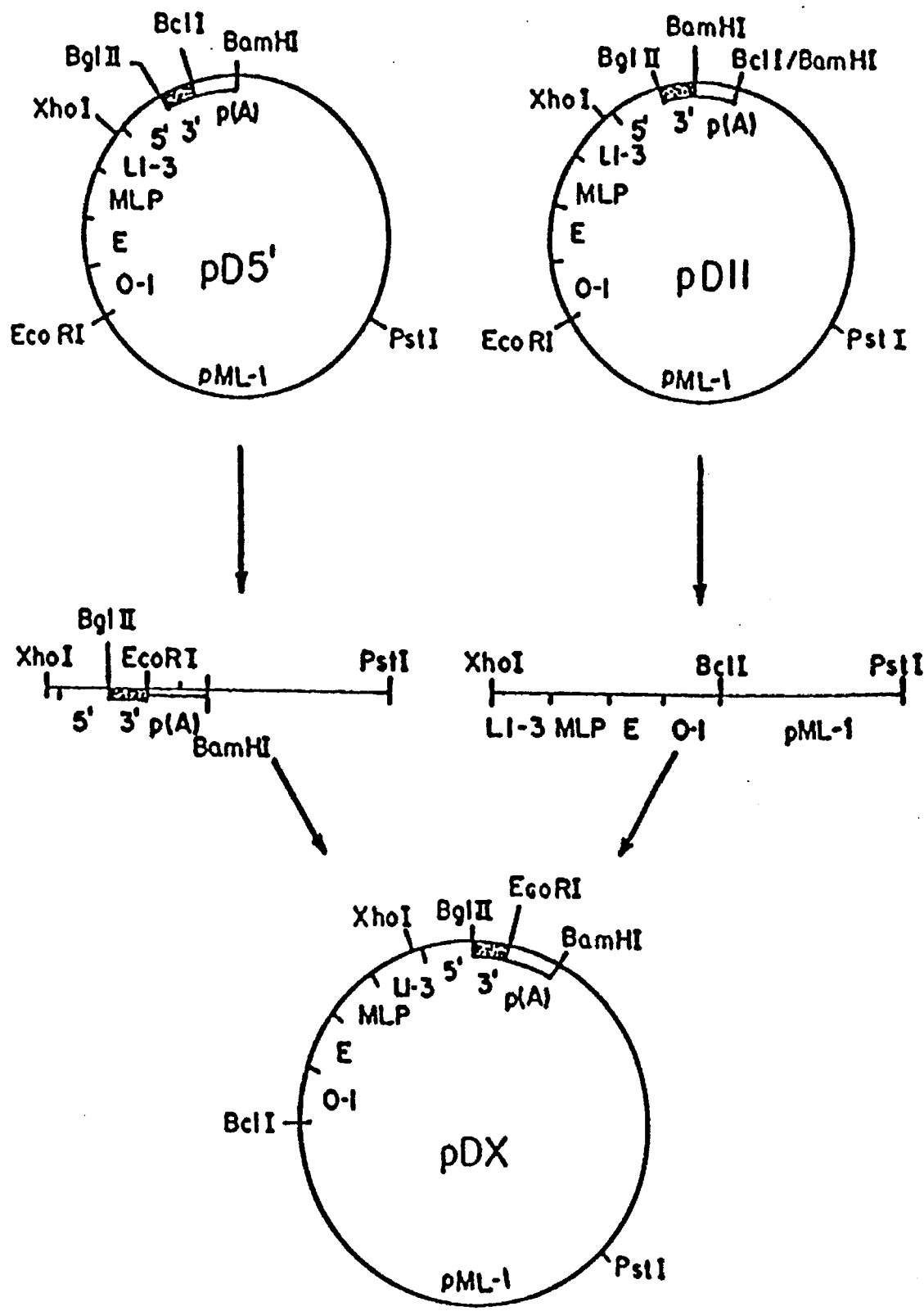
FIG. 12 illustrates the construction of the vector pDX. Symbols are used as set forth for FIG. 10.

To generate pDX, the Eco RI site in pD11 was converted to a Bcl I site by Eco RI cleavage, incubation with S1 nuclease, and subsequent ligation with Bcl I linkers. DNA was prepared from a positively identified colony, and the 1.9 kb Xho I-Pst I fragment containing the altered restriction site was prepared via agarose gel electrophoresis. In a second modification, Bcl I-cleaved pD5' was ligated with kinased Eco RI-Bcl I adapters (constructed from oligonucleotides ZC525, 5'GGAATTCT3'; and ZC526, 5'GATCAGAATTCC3') in order to generate an Eco RI site as the position for inserting a gene into the expression vector. Positive colonies were identified by restriction endonuclease analysis, and DNA from this was used to isolate a 2.3 kb Xho I-Pst I fragment containing the modified restriction site. The two above-described DNA fragments were incubated together with T$_4$ DNA ligase, transformed into *E. coli* HB101 and positive colonies were identified by restriction analysis. A preparation of such DNA, termed pDX (FIG. 12), was then made. This plasmid contains a unique Eco RI site for insertion of foreign genes.

The protein C cDNA was then inserted into pDX as an Eco RI fragment. Recombinant plasmids were screened by restriction analysis to identify those having the protein C insert in the correct orientation with respect to the promoter elements, and plasmid DNA (designated pDX/PC) was prepared from a correct clone. Because the cDNA insert in pDX/PC contains an ATG codon in the 5' noncoding region, deletion mutagenesis was performed on the cDNA prior to transfection and expression experiments. Deletion of the three base pairs was performed according to standard procedures of oligonucleotide-directed mutagenesis. The pDX-based vector containing the modified cDNA was designated p594.

D. Expression of Protein C in a KEX2 Transfected Cell Line

Figure 13:
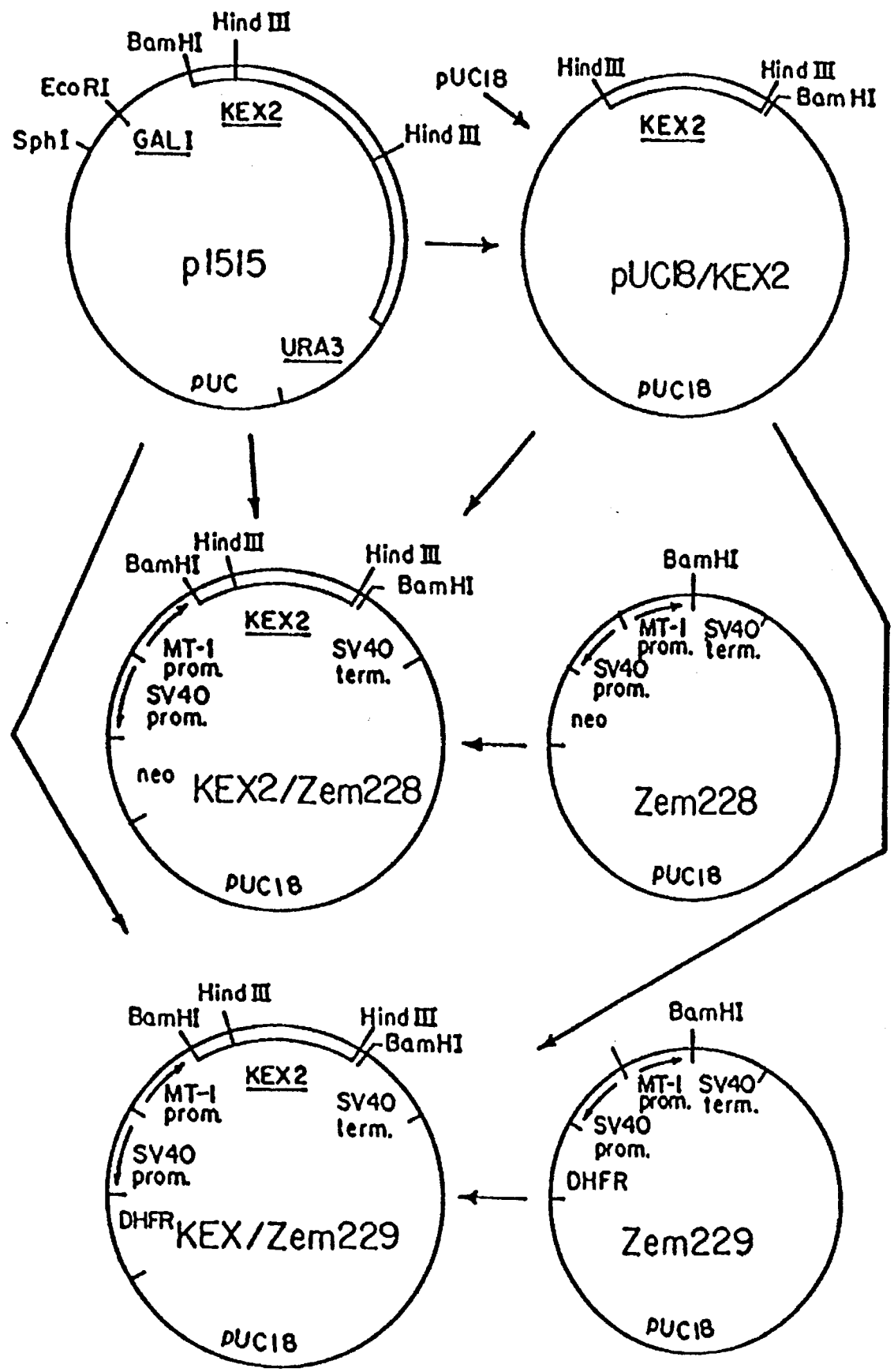
FIG. 13 illustrates the construction of expression vectors containing the S. cerevisiae KEX2 gene.

The *Saccharomyces cerevisiae* KEX2 gene was isolated from a yeast genomic library by screening transformed kex2 mutant cells for production of an α-factor halo on a lawn of suitable tester cells. One clone was obtained which complemented all reported defects of kex2 mutations (mating, α-factor production, maturation of killer toxin and sporulation in a kex2 homozygous diploid strain). The gene was subcloned into a pUC vector under the control of the yeast GAL1 promoter. The resultant plasmid, designated p1515, has been deposited with American Type Culture Collection as an *E. coli* HB101 transformant under accession number 67569. As shown in FIG. 13, p1515 was digested with Hind III and a 2.1 kb fragment was recovered. This fragment was ligated to Hind III-cut pUC18 to construct plasmid pUC18/KEX2. The KEX2 fragment (2.1 kb) was then isolated from pUC18/KEX2 by digesting the plasmid partially with Hind III and to completion with Bam HI. The remainder of the KEX2 sequence was then isolated as a 0.43 kb fragment from a Bam HI+Hind III digest of p1515. The two KEX2 fragments were then ligated into the Bam HI site of the vectors Zem228 and Zem229 (FIG. 13). The resulting plasmids were designated KEX2/Zem228 and KEX2/Zem229, respectively.

The BHK 570 cell line was cotransfected with the plasmids p594 and pSV2-DHFR by the calcium phosphate procedure. Transfected cells were selected with 250 nM methotrexate (MTX) and clonal cell lines were isolated. A clonal cell line which secreted protein C into the culture medium at 1.5 pg/cell/day was selected and designated PC594-204/BHK.

Ten μg of KEX2/Zem228 was transfected into the PC594-204/BHK cell line by the calcium phosphate procedure. Cells were cultured in the presence of 250 nM MTX at all times. Clones were selected with 500 μg/ml G418 and twelve clonal cell lines were selected.

The selected clones were pulse-labeled with $^{35}$S-cysteine in cysteine-free MEM (Gibco) containing 1% fetal calf serum for 24 hours. The culture media were collected and examined for the presence of single-chain and cleaved two-chain protein C by immunoprecipitation with a monoclonal antibody to protein C. 250 μof media was combined with 10 μg of the antibody and the mixture was incubated at 37° C. for one hour. 100 μl of Staph A cell suspension (Pharmacia, Piscataway, N.J.) was added and incubation was continued at 37° C. for one hour. The cells were pelleted by centrifugation, and the pellet was resuspended in TBS. The cells were again pelleted, and the pellet was resuspended in 60 μl of gel buffer containing 1% β-mercaptoethanol. The suspension was heated to 100° C. for three minutes, then electrophoresed on an SDS-polyacrylamide gel. Proteins were visualized by autoradiography. The parent cell line, PC594-204, showed approximately 70% of the protein C in the one-chain form, with the remaining 30% in the two-chain form. One of the G418-selected KEX2 cell lines, designated PC594-204/KEX21, produced 95% two-chain protein C, with the remaining 5% in the one-chain form.

Example 4

Co-expression of Coagulation Factors VII and IX

Plasmid FIX/pD2 (Busby et al., *Nature* 316:271–273, 1985) was digested with Bam HI and the 1.4 kb factor IX fragment was recovered. This fragment was then joined to pD5' which had been digested with Bam HI and treated with calf intestinal phosphatase. The resultant plasmid was designated FIX/pD5'.

Figure 14:
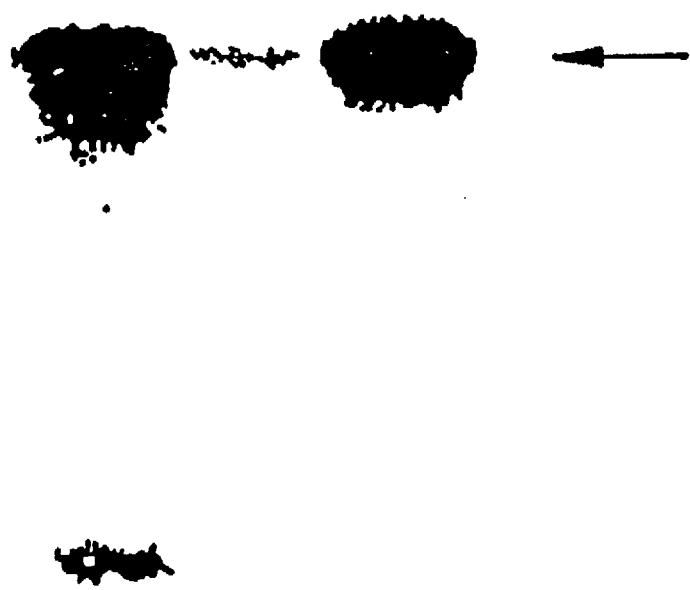
FIG. 14 shows the results of a radioimmune precipitation of factor VII produced by cells co-expressing factor IX (lane 1) and by factor VII-transfected control cells (lane 2). The arrow indicates the position of single-chain factor VII.

To co-express factor VII and factor IX, 10 μg of FIX/pD5', 10 μg of FVII (565+2463)/pDX (U.S. Pat. No. 4,784,950; ATCC 40205) and 1 μg of DHFR$^{res}$-pD5' (a pD5'-derived plasmid containing a methotrexate resistant DHFR gene [Levinson et al., EP 117,060]) were used to transfect BHK 570 cells. Transfected cells were selected in the presence of methotrexate, then assayed for production of factor VII and factor IX by immunofilter assay using antibodies to both proteins. Colonies which were positive for both factor VII and factor IX production were selected, grown up and pulsed with $^{35}$S-cysteine. Culture media and intracellular proteins were immunoprecipitated with the factor VII and IX antibodies and analyzed by polyacrylamide gel electrophoresis. Cells co-expressing factor VII and factor IX produced two-chain factor VII (i.e., factor VIIa). In contrast, cells producing only factor VII showed only the single-chain form of the protein (FIG. 14).

Example 5

Co-expression in *Saccharomyces cerevisiae*

The *S. cerevisiae* BAR1 gene encodes a secreted protein known as Barrier. The secretory peptide portion of the BAR1 gene product or the secretory peptide plus the third (C-terminal) domain of Barrier may be used to facilitate the secretion of foreign proteins produced in *S. cerevisiae*.

As described in U.S. patent application Ser. No. 07/086,040, an expression vector containing the sequences encoding the signal peptide and third domain of Barrier fused to the coding sequence for the B(1-29)-Ala-Ala-Lys-A(1-21) insulin precursor (Markussen et al., EP 163,529) was constructed. This vector, designated pSW195 (FIG. 15), also contains the yeast TPI1 promoter and terminator. The Barrier and insulin sequences are joined at the amino acid sequence lys-arg. To allow processing of the fusion protein by thrombin, the lys-arg junction sequence was mutagenized to pro-arg. Cleavage at this site by thrombin will result in secretion of the unfused insulin precursor.

Figure 15:
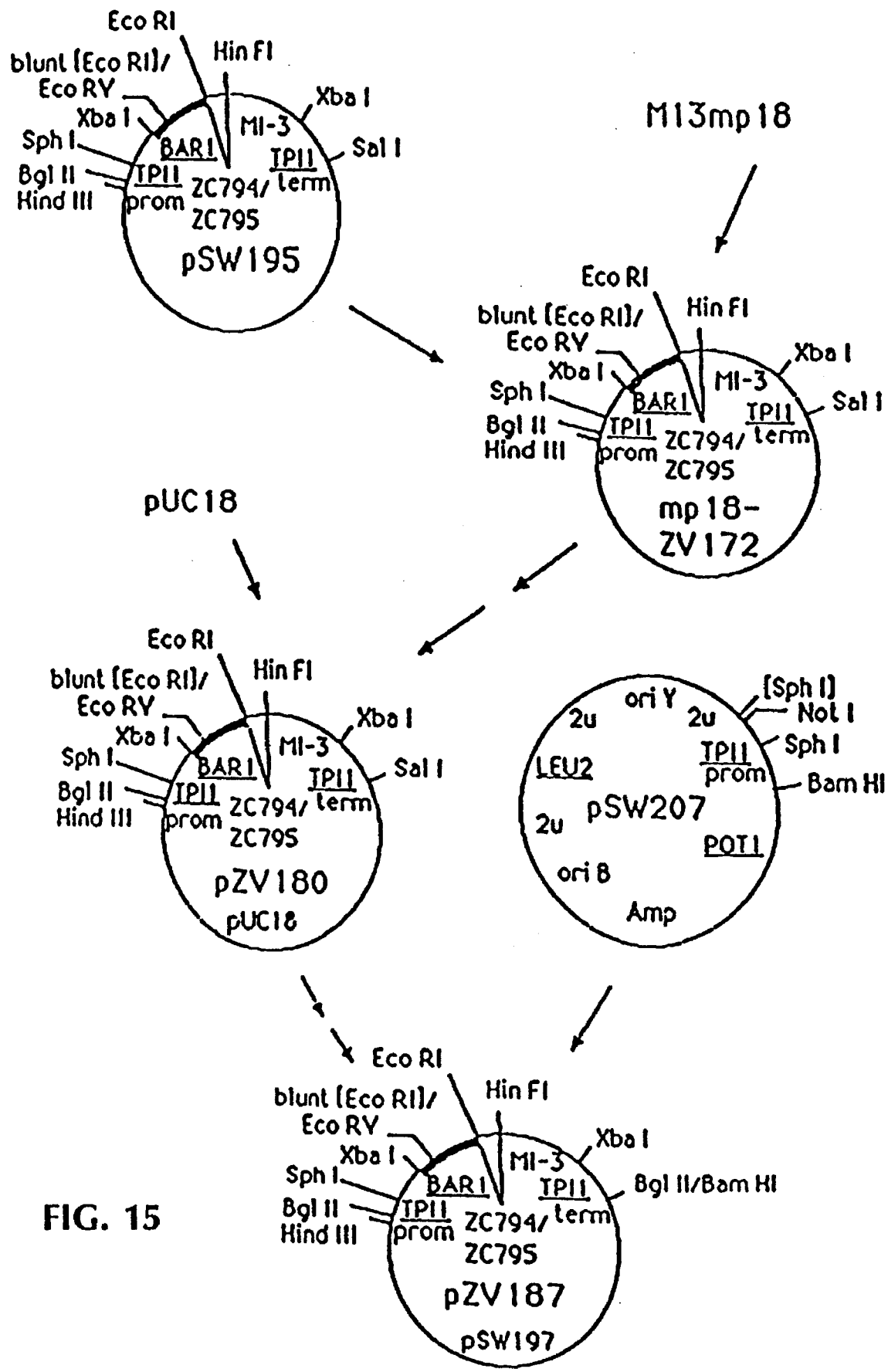
FIG. 15 illustrates the construction of a yeast expression vector containing a DNA sequence encoding a thrombin-cleavable fusion protein. "MI-3" indicates the insulin precursor DNA sequence.

As shown in FIG. 15, plasmid pSW195 was digested with Sph I and Sal I to isolate the 1.7 kb fragment comprising the BAR1-insulin fusion and the TPI1 terminator. This fragment was ligated with M13mp18 which had been previously digested to completion with Sph I and Sal I. The resultant phage clone was designated mp18-ZV172. Oligonucleotide ZC1083 (5'TCC TTG GAT CCA AGA TTC GTT$^{3'}$) was used to mutagenize mp18-ZV172 using the uracil method (Kunkel, *Proc. Natl. Acad. Sci. USA* 82:488–492, 1985). The resultant mutants were sequenced to confirm the mutagenesis and a positive clone was designated ZV172/1083. For convenience, the insert present in ZV172/1083 was subcloned into pUC18. The 1.7 kb Sph I-Sal I insert from ZV172/1083 was isolated and ligated with pUC18 which had been previously digested to completion with Sph I and Sal I. The resultant plasmid, pZV180, was digested to completion with Sal I. The adhesive ends of the linearized pZV180 were blunted using DNA polymerase I (Klenow fragment) and ligated to kinased Bgl II linkers. Excess linkers were removed by digestion with Bgl II. The linkered DNA was then cut to completion with Sph I to isolate the 1.7 kb insert. The 1.7 kb insert, comprising the partial TPI1 promoter, the BAR1-MI-3 fusion and the TPI1 terminator, was ligated into the Sph I-Bam HI partial TPI1 promoter-vector fragment of plasmid pSW207 to construct pZV187. (pSW207 was derived from pCPOT [ATCC 39685] by replacing the 750 bp Sph I-Bam HI fragment of pCPOT, containing 2 micron and pBR322 sequences, with a 186 bp Sph I-Bam HI fragment derived from the pBR322 tetracycline resistance gene; destroying the Sph I site and inserting a Not I site in the tetracycline resistance gene; digesting the resultant plasmid with Not I and Bam HI; and inserting a Not I-Bam HI TPI1 promoter fragment in place of the Not I-Bam HI pBR322-derived sequence.)

The thrombin cDNA is isolated from a prothrombin cDNA cloned in the Pst I site of pBR322 (Friezner Degan et al., ibid.). The KEX2 gene from p1515 (Example 3) is digested and manipulated to remove the catalytic domain and the remaining sequences are joined to the thrombin cDNA. An expression unit is prepared by joining the hybrid gene to the TPI1 promoter and terminator. This expression unit is then substituted for the coding region of the yeast BAR1 gene. The resultant construct, comprising the expression unit flanked by BAR1 gene noncoding sequences, is used to transform *S. cerevisiae*. The transformed cells are cultured and screened for production of thrombin by enzyme activity assay. A colony positive for thrombin production is then transformed with pZV187. Cells are cultured, and the insulin precursor is isolated from the media.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:
1. A method for producing a protein of interest, comprising;

introducing into a eukaryotic host cell a first DNA sequence encoding plasminogen and at least one additional DNA sequence, said additional DNA sequence encoding a protein which processes or stabilizes the plasminogen selected from the group consisting of alpha-1-antitrypsin variant thereof, and an Argserpin, wherein said DNA sequences are operably linked to transcriptional promoter and terminator sequences;

culturing the host cell under conditions which allow the first DNA sequence and the additional DNA sequence (s) to be expressed; and isolating the plasminogen from the host cell.

2. The method of claim 1 wherein the step of introducing comprises cotransfecting or cotransforming the host cell with multiple vectors, each containing a separate expression unit.

3. The method of claim 1 wherein the step of introducing comprises transfecting or transforming the host cell with a single vector containing multiple expression units.

4. The method of claim 1 wherein the host cell is a mammalian cell and the step of introducing comprises transfecting the host cell with a single vector containing a single expression unit that is transcribed into a polycistronic message.

5. The method of claim 1 wherein the host cell is a yeast cell and the additional DNA sequence is integrated into the genome of the host cell.

6. The method of claim 1 wherein the eukaryotic host cell is a mammalian host cell or a yeast host cell.

7. The method of claim 1 wherein the eukaryotic host cell is a cultured mammalian cell.

8. The method of claim 1 including, after the step of isolating, purifying the protein of interest.

9. The method of claim 8 wherein the step purifying is by affinity chromatography, ion exchange chromatography, gel filtration, high performance liquid chromatography, or combinations thereof.

10. A eukaryotic host cell transfected or transformed to express a first DNA sequence encoding plasminogen and at least one additional DNA sequence, said additional DNA sequence encoding a protein which processes or stabilizes the plasminogen selected from the group consisting of alpha-1-antitrypsin, variant thereof, and an Argserpin.

11. The host cell of claim 10 wherein the eukaryotic host cell is a mammalian host cell or a yeast host cell.

12. The host cell of claim 10 wherein said cell is a cultured mammalian cell.

13. The host cell of claim 10, wherein said cell is a baby hamster kidney cell.

14. A method for producing plasminogen, comprising:
introducing into a baby hamster kidney cell a first DNA sequence encoding plasminogen and an additional DNA sequence encoding a protein selected from the group consisting of Arg(358) alpha-1-antitrypsin, $\alpha_2$ plasmin inhibitor and plasminogen activator inhibitor 1, wherein said DNA sequences are operably linked to transcriptional promoter and terminator sequences;
culturing the cell under conditions which allow the first and additional DNA sequences to be expressed; and
isolating the plasminogen from the cell.

15. A baby hamster kidney cell transfected to express a DNA sequence encoding plasminogen and a DNA sequence encoding a protein selected from the group consisting of Arg(385) alpha-1-antitrypsin $\alpha_2$ plasmin inhibitor and plasminogen activator inhibitor 1.

* * * * *